United States Patent
Chen et al.

(10) Patent No.: US 7,120,490 B2
(45) Date of Patent: *Oct. 10, 2006

(54) CARDIAC RHYTHM MANAGEMENT SYSTEM WITH ATRIAL SHOCK TIMING OPTIMIZATION

(75) Inventors: Victor T. Chen, Minnetrista, MN (US); Jay A. Warren, North Oaks, MN (US); Gary T. Seim, Minneapolis, MN (US); David B. Krig, Brooklyn Park, MN (US); Jesse W. Hartley, Lino Lakes, MN (US); Jeffrey E. Stahmann, Ramsey, MN (US)

(73) Assignee: Cardiac Pacemakers, Inc., Saint Paul, MN (US)

(*) Notice: Subject to any disclaimer, the term of this patent is extended or adjusted under 35 U.S.C. 154(b) by 0 days.

This patent is subject to a terminal disclaimer.

(21) Appl. No.: 10/211,414

(22) Filed: Aug. 2, 2002

(65) Prior Publication Data

US 2003/0004551 A1 Jan. 2, 2003

Related U.S. Application Data

(63) Continuation of application No. 09/316,741, filed on May 21, 1999, now Pat. No. 6,430,438.

(51) Int. Cl.
*A61N 1/39* (2006.01)
(52) U.S. Cl. .......................................................... 607/4
(58) Field of Classification Search .................... 607/4, 607/5, 9, 14
See application file for complete search history.

(56) References Cited

U.S. PATENT DOCUMENTS 3,857,399 A 12/1974 Zacouto .................. 128/419 P
4,030,510 A 6/1977 Bowers ................. 128/419 PG (Continued)

FOREIGN PATENT DOCUMENTS

EP 0033418 12/1980

(Continued)

OTHER PUBLICATIONS

Mehra, R..,et al. , "Prevention of Atrial Fibrillation/Flutter by Pacing techniques", *Interventional Electrophysiology, Second Edition*, Chaper 34, Futura Publishing Company, Inc., (1996),pp. 521-540.

(Continued)

*Primary Examiner*—George R. Evanisko
(74) *Attorney, Agent, or Firm*—Schwegman, Lundberg, Woessner & Kluth, P.A.

(57) ABSTRACT

A cardiac rhythm management system includes atrial shock timing optimization. Because an atrial tachyarrhythmia, such as atrial fibrillation typically causes significant variability in the ventricular heart rate, resulting in potentially proarrhythmic conditions. The system avoids delivering atrial cardioversion/defibrillation therapy during potentially proarrhythmic conditions because doing so could result in dangerous ventricular arrhythmias. Using Ventricular Rate Regularization ("VRR") techniques, the system actively stabilizes the ventricular heart rate to obtain less potentially proarrhythmic conditions for delivering the atrial tachyarrhythmia therapy. The intrinsic ventricular heart rate is stabilized at a variable VRR-indicated rate, computed using an infinite impulse response (IIR) filter, and based on the underlying intrinsic ventricular heart rate. The system withholds delivery of atrial cardioversion/defibrillation therapy until the intervals between ventricular beats ("V—V intervals") meet certain criteria that decrease the chance that the atrial cardioversion/defibrillation therapy will induce a ventricular arrhythmia.

32 Claims, 21 Drawing Sheets

U.S. PATENT DOCUMENTS

| | | | |
|---|---|---|---|
| 4,163,451 A | 8/1979 | Lesnick et al. ........ 128/419 PG |
| RE30,387 E | 8/1980 | Denniston, III et al. .... 128/419 |
| 4,503,857 A | 3/1985 | Boute et al. .......... 128/419 PG |
| 4,554,922 A | 11/1985 | Prystowsky et al. ........ 128/419 |
| 4,556,063 A | 12/1985 | Thompson et al. .... 128/419 PT |
| 4,787,389 A | 11/1988 | Tarjan |
| 4,830,006 A | 5/1989 | Haluska et al. ................. 607/4 |
| 4,869,252 A | 9/1989 | Gilli ..................... 128/419 PG |
| 4,905,697 A | 3/1990 | Heggs et al. ......... 128/419 PG |
| 4,917,115 A | 4/1990 | Flammang et al. ... 128/419 PG |
| 4,920,965 A | 5/1990 | Funke et al. .......... 128/419 PG |
| 4,928,688 A | 5/1990 | Mower ................. 128/419 PG |
| 4,940,054 A | 7/1990 | Grevis et al. ......... 128/419 PG |
| 4,944,298 A | 7/1990 | Sholder ................ 128/419 PG |
| 4,945,909 A | 8/1990 | Fearnot et al. ........ 128/419 PG |
| 4,998,974 A | 3/1991 | Aker ..................... 128/419 PG |
| 5,012,814 A | 5/1991 | Mills et al. ................. 128/691 |
| 5,042,480 A | 8/1991 | Hedin et al. .......... 128/419 PG |
| 5,077,667 A * | 12/1991 | Brown et al. ................... 607/5 |
| 5,085,215 A | 2/1992 | Nappholz et al. ..... 128/419 PG |
| 5,101,824 A | 4/1992 | Lekholm .............. 128/419 PG |
| 5,107,850 A | 4/1992 | Olive ........................... 128/705 |
| 5,127,404 A | 7/1992 | Wyborny et al. ........ 128/419 P |
| 5,129,394 A | 7/1992 | Mehra ................. 128/419 PG |
| 5,139,020 A | 8/1992 | Koestner et al. ...... 128/419 PG |
| 5,144,949 A | 9/1992 | Olson ................... 128/419 PG |
| 5,156,147 A | 10/1992 | Warren et al. ......... 128/419 PG |
| 5,156,154 A | 10/1992 | Valenta, Jr. et al. .... 128/661.09 |
| 5,179,945 A | 1/1993 | Van Hofwegen et al. |
| 5,183,040 A | 2/1993 | Nappholz et al. ..... 128/419 PG |
| 5,184,614 A | 2/1993 | Collins et al. ......... 128/419 PG |
| 5,188,105 A | 2/1993 | Keimel |
| 5,188,106 A | 2/1993 | Nappholz et al. ..... 128/419 PG |
| 5,193,535 A | 3/1993 | Bardy et al. ............. 128/419 D |
| 5,193,550 A | 3/1993 | Duffin ........................ 129/697 |
| 5,207,219 A | 5/1993 | Adams et al. ........... 128/419 D |
| 5,282,836 A | 2/1994 | Kreyenhagen et al. ......... 607/4 |
| 5,284,491 A | 2/1994 | Sutton et al. .................. 607/17 |
| 5,292,338 A | 3/1994 | Bardy |
| 5,292,339 A | 3/1994 | Stephens et al. ............... 607/15 |
| 5,311,874 A | 5/1994 | Baumann et al. ........... 128/705 |
| 5,312,452 A | 5/1994 | Salo ............................. 607/17 |
| 5,325,856 A | 7/1994 | Nitzsche et al. |
| 5,331,966 A | 7/1994 | Bennett et al. ............. 128/696 |
| 5,332,400 A | 7/1994 | Alferness ........................ 607/5 |
| 5,334,220 A | 8/1994 | Sholder ........................... 607/9 |
| 5,350,406 A | 9/1994 | Nitzsche et al. |
| 5,350,409 A | 9/1994 | Stoop et al. .................. 607/17 |
| 5,356,425 A | 10/1994 | Bardy et al. .................. 607/14 |
| 5,365,932 A | 11/1994 | Greenhut .................... 128/696 |
| 5,366,485 A | 11/1994 | Kroll et al. |
| 5,379,776 A | 1/1995 | Murphy et al. |
| 5,383,910 A | 1/1995 | den Dulk .................... 607/14 |
| 5,391,189 A | 2/1995 | van Krieken et al. ......... 607/17 |
| 5,395,373 A | 3/1995 | Ayers ............................. 607/8 |
| 5,395,397 A | 3/1995 | Lindgren et al. ............... 607/9 |
| 5,400,796 A | 3/1995 | Wecke ........................ 128/705 |
| 5,411,524 A | 5/1995 | Rahul ............................. 607/4 |
| 5,411,531 A | 5/1995 | Hill et al. ..................... 607/14 |
| 5,417,714 A | 5/1995 | Levine et al. .................. 607/9 |
| 5,423,869 A | 6/1995 | Poore et al. ................. 607/18 |
| 5,437,285 A | 8/1995 | Verrier et al. .............. 128/702 |
| 5,462,060 A | 10/1995 | Jacobson et al. ............ 128/702 |
| 5,474,574 A | 12/1995 | Payne et al. ................... 607/7 |
| 5,480,413 A | 1/1996 | Greenhut et al. ............ 607/14 |
| 5,486,198 A * | 1/1996 | Ayers et al. ................... 607/5 |
| 5,487,752 A | 1/1996 | Salo et al. .................... 607/17 |
| 5,489,293 A | 2/1996 | Pless et al. |
| 5,507,782 A | 4/1996 | Kieval et al. .................. 607/9 |
| 5,507,784 A | 4/1996 | Hill et al. ..................... 607/14 |
| 5,514,163 A | 5/1996 | Markowitz et al. ............ 607/9 |
| 5,522,850 A | 6/1996 | Yomtov et al. ................. 607/5 |
| 5,522,859 A | 6/1996 | Stroebel et al. ............... 607/19 |
| 5,527,347 A | 6/1996 | Shelton et al. .................. 607/9 |
| 5,531,768 A | 7/1996 | Alferness |
| 5,534,016 A | 7/1996 | Boute ............................. 607/9 |
| 5,540,727 A | 7/1996 | Tockman et al. ............. 607/18 |
| 5,545,182 A | 8/1996 | Stotts et al. .................... 607/5 |
| 5,545,186 A | 8/1996 | Olson et al. .................. 607/14 |
| 5,554,174 A | 9/1996 | Causey, III .................... 607/5 |
| 5,560,369 A | 10/1996 | McClure et al. ............ 128/704 |
| 5,584,864 A | 12/1996 | White ............................ 607/5 |
| 5,584,867 A | 12/1996 | Limousin et al. .............. 607/9 |
| 5,591,215 A | 1/1997 | Greenhut et al. ............ 607/14 |
| 5,605,159 A | 2/1997 | Smith et al. ................ 128/702 |
| 5,613,495 A | 3/1997 | Mills et al. ................. 128/696 |
| 5,626,620 A | 5/1997 | Kieval et al. .................. 607/9 |
| 5,626,622 A | 5/1997 | Cooper ........................ 607/18 |
| 5,626,623 A | 5/1997 | Kieval et al. ................ 607/23 |
| 5,632,267 A | 5/1997 | Hognelid et al. .............. 607/5 |
| 5,674,250 A | 10/1997 | de Coriolis et al. ............ 607/7 |
| 5,674,251 A | 10/1997 | Combs et al. .................. 607/4 |
| 5,674,255 A | 10/1997 | Walmsley et al. ............ 607/14 |
| 5,676,153 A | 10/1997 | Smith et al. ................ 128/702 |
| 5,683,429 A | 11/1997 | Mehra ......................... 607/14 |
| 5,690,689 A | 11/1997 | Sholder ....................... 607/24 |
| 5,700,283 A | 12/1997 | Salo ............................ 607/17 |
| 5,713,929 A | 2/1998 | Hess et al. ................... 607/14 |
| 5,713,930 A | 2/1998 | van der Veen et al. ....... 607/25 |
| 5,713,932 A | 2/1998 | Gillberg et al. .............. 607/27 |
| 5,716,383 A | 2/1998 | Kieval et al. .................. 607/9 |
| 5,718,235 A | 2/1998 | Golosarsky et al. ........ 128/708 |
| 5,725,561 A | 3/1998 | Stroebel et al. ................. 607/9 |
| 5,730,141 A | 3/1998 | Fain et al. .................. 128/705 |
| 5,730,142 A | 3/1998 | Sun et al. ................... 128/705 |
| 5,738,096 A | 4/1998 | Ben-Haim ............... 128/653.1 |
| 5,741,304 A | 4/1998 | Patwardhan et al. ........... 607/5 |
| 5,741,308 A | 4/1998 | Sholder ......................... 607/9 |
| 5,749,901 A | 5/1998 | Bush et al. ..................... 607/5 |
| 5,749,906 A | 5/1998 | Kieval et al. .................. 607/9 |
| 5,755,736 A | 5/1998 | Gillberg et al. ................ 607/4 |
| 5,755,737 A | 5/1998 | Prieve et al. ................... 607/4 |
| 5,755,739 A | 5/1998 | Sun et al. ..................... 607/14 |
| 5,755,740 A | 5/1998 | Nappholz ................... 607/18 |
| 5,759,196 A | 6/1998 | Hess et al. ................... 607/14 |
| 5,772,604 A | 6/1998 | Langberg et al. |
| 5,776,164 A | 7/1998 | Ripart ............................ 607/5 |
| 5,776,167 A | 7/1998 | Levine et al. .................. 607/9 |
| 5,788,717 A | 8/1998 | Mann et al. .................. 607/14 |
| 5,792,193 A | 8/1998 | Stoop .......................... 607/14 |
| 5,800,464 A | 9/1998 | Kieval ........................... 607/9 |
| 5,800,471 A | 9/1998 | Baumann .................... 607/25 |
| 5,814,077 A | 9/1998 | Sholder et al. ................. 607/9 |
| 5,814,081 A | 9/1998 | Ayers et al. ................... 607/5 |
| 5,814,085 A | 9/1998 | Hill ............................. 607/14 |
| 5,836,975 A | 11/1998 | DeGroot ........................ 607/5 |
| 5,836,987 A | 11/1998 | Baumann et al. ............ 607/17 |
| 5,840,079 A | 11/1998 | Warman et al. ................ 607/4 |
| 5,842,997 A | 12/1998 | Verrier et al. .............. 600/518 |
| 5,846,263 A | 12/1998 | Peterson et al. ............. 607/14 |
| 5,853,426 A | 12/1998 | Shieh ............................ 607/5 |
| 5,855,593 A | 1/1999 | Olson et al. .................... 607/9 |
| 5,861,007 A | 1/1999 | Hess et al. ..................... 607/9 |
| 5,865,838 A | 2/1999 | Obel et al. ..................... 607/5 |
| 5,873,895 A | 2/1999 | Sholder et al. ................. 607/9 |
| 5,873,897 A | 2/1999 | Armstrong et al. ........... 607/14 |
| 5,893,882 A | 4/1999 | Peterson et al. ............. 607/14 |
| 5,897,575 A | 4/1999 | Wickham ...................... 607/4 |
| 5,916,239 A | 6/1999 | Geddes et al. |
| 5,928,271 A | 7/1999 | Hess et al. ................... 607/14 |
| 5,931,857 A | 8/1999 | Prieve et al. ................. 607/14 |
| 5,935,081 A | 8/1999 | Kadhiresan ................ 600/513 |
| 5,944,744 A | 8/1999 | Paul et al. ...................... 607/9 |
| 5,951,592 A | 9/1999 | Murphy ......................... 607/4 |

| | | | |
|---|---|---|---|
| 5,968,079 A | 10/1999 | Warman et al. | 607/5 |
| 5,978,707 A | 11/1999 | Krig et al. | 607/14 |
| 5,978,710 A | 11/1999 | Prutchi et al. | 607/17 |
| 5,983,138 A | 11/1999 | Kramer | 607/9 |
| 5,987,354 A | 11/1999 | Cooper et al. | 607/5 |
| 5,987,356 A | 11/1999 | DeGroot | 607/5 |
| 5,991,656 A | 11/1999 | Olson et al. | 607/4 |
| 5,991,657 A | 11/1999 | Kim | 607/5 |
| 5,991,662 A | 11/1999 | Kim et al. | 607/27 |
| 5,999,850 A * | 12/1999 | Dawson et al. | 607/4 |
| 5,999,854 A * | 12/1999 | Deno et al. | 607/18 |
| 6,026,320 A | 2/2000 | Carlson et al. | 600/510 |
| 6,041,251 A | 3/2000 | Kim et al. | 600/518 |
| 6,044,298 A | 3/2000 | Salo et al. | 607/17 |
| 6,047,210 A | 4/2000 | Kim et al. | 607/4 |
| 6,049,735 A | 4/2000 | Hartley et al. | 607/9 |
| 6,052,617 A | 4/2000 | Kim | 600/518 |
| 6,052,620 A | 4/2000 | Gillberg et al. | 607/4 |
| 6,058,328 A | 5/2000 | Levine et al. | 607/14 |
| 6,081,745 A * | 6/2000 | Mehra | 607/4 |
| 6,081,746 A | 6/2000 | Pendekanti et al. | 607/5 |
| 6,081,747 A | 6/2000 | Levine et al. | 607/9 |
| RE36,765 E | 7/2000 | Mehra | 607/4 |
| 6,085,116 A | 7/2000 | Pendekanti et al. | 607/5 |
| 6,091,988 A | 7/2000 | Warman et al. | 607/5 |
| 6,151,524 A | 11/2000 | Krig et al. | |
| 6,246,906 B1 | 6/2001 | Hsu et al. | 607/4 |
| 6,246,909 B1 | 6/2001 | Ekwall | 607/9 |
| 6,249,699 B1 | 6/2001 | Kim | 607/4 |
| 6,256,534 B1 | 7/2001 | Dahl | 607/5 |
| 6,272,380 B1 | 8/2001 | Warman et al. | 607/5 |
| 6,275,734 B1 * | 8/2001 | McClure et al. | 607/27 |
| 6,280,391 B1 * | 8/2001 | Olson et al. | 607/5 |
| 6,285,907 B1 | 9/2001 | Kramer et al. | 607/9 |
| 6,292,694 B1 | 9/2001 | Schloss et al. | |
| 6,317,632 B1 | 11/2001 | Krig et al. | 607/14 |
| 6,353,759 B1 | 3/2002 | Hartley et al. | 607/9 |
| 6,408,209 B1 | 6/2002 | Bouhour et al. | 607/19 |
| 6,411,847 B1 | 6/2002 | Mower | 607/9 |
| 6,411,848 B1 | 6/2002 | Kramer et al. | 607/9 |
| 6,430,438 B1 * | 8/2002 | Chen et al. | 607/5 |
| 6,434,424 B1 | 8/2002 | Igel et al. | 607/9 |
| 6,501,987 B1 | 12/2002 | Lovett et al. | 607/9 |
| 6,501,988 B1 | 12/2002 | Kramer et al. | 607/9 |
| 6,512,951 B1 | 1/2003 | Marcovecchio et al. | 607/5 |
| 6,526,317 B1 | 2/2003 | Hsu et al. | 607/4 |
| 6,584,350 B1 | 6/2003 | Kim | 607/5 |
| 6,687,541 B1 | 2/2004 | Marcovecchio et al. | |
| 6,721,596 B1 | 4/2004 | Girouard et al. | 607/4 |
| 6,847,842 B1 | 1/2005 | Rodenhiser et al. | |
| 2003/0199928 A1 | 10/2003 | Hsu et al. | 607/5 |
| 2004/0015192 A1 | 1/2004 | Kim et al. | 607/5 |
| 2004/0172076 A1 | 9/2004 | Stahmann et al. | |
| 2004/0215259 A1 | 10/2004 | Tarjan | |

FOREIGN PATENT DOCUMENTS

| | | |
|---|---|---|
| WO | WO-93/02746 | 2/1993 |
| WO | WO-95/09029 | 4/1995 |
| WO | WO-97/11745 | 4/1997 |
| WO | WO-98/48891 | 11/1998 |
| WO | WO-00/09206 | 2/2000 |
| WO | WO-00/71200 | 11/2000 |
| WO | WO-00/71203 | 11/2000 |
| WO | WO-0071202 | 11/2000 |

OTHER PUBLICATIONS

Wittkampf, F.H.M.., et al., "Rate Stabilization by Right Ventricular Patching on Patients with Atrial Fibrillation",*Pace*, 9, (Nov.-Dec., 1986), 1147-1153.

*Metrix Model 3020 Implantable Atrial Defibrillator*, Physician's Manual, InControl, Inc, Redmond, WA, (1998), pp. 4-24 - 4-27.

*Harmony, Automatic Dual Chamber Pacemaker, Product Information and Programming Guide*, Viatron Medical, Harmony Dual Chamber mentioned in public Clinica, 467, p. 16, (Sep. 11, 1991), "Rate Devices Impact Pacemaker Market", and Clinica, 417, p. 9, (Sep. 5, 1990), "French CNH Equiptment Approvals"., 22 p.

Ayers, Gregory. M.,et al., "Ventricular Proarrhythmic Effects of Ventricular Cycle Length and Shock Strength in a Sheep Model of Transvenous Atrial Defibrillation", *Circulation*, 89 (1). (Jan. 1994), pp. 413-422.

Duckers, H..J.,et al.,"Effective use of a novel rate-smoothing algorithm in atrial fibrillation by ventricular pacing", *European Heart Journal*, 18, (1997),pp. 1951-1955.

Fahy, G..J.,et al.,"Pacing Strategies to Prevent Atrial Fibrillation", *Atrial Fibrillation*, 14 (4), (Nov. 1996), pp. 591-596.

Greenhut, S., et al., "Effectiveness of a Ventriicular Rate Stabilization Algorithm During Atrial Fibrillation in Dogs ", *Pace Abstract*, Abstract No. 60, (1996), 1 p.

Heuer, H. ,et al. ,"Dynamic Dual-Chamber Overdrive Pacing with an Implantable Pacemaker System: A New Method for Terminating Slow Ventricular Tachycardia", *Zeitschrif fur Kardiologie*, 75, German Translation by the Ralph McElroy Translation Company, Austin, TX, (1986),5 p.

Wittkampf, F.H.M. ,et al. ,"Rate Stabilization by Right Ventricular Pacing in Patients with Atrial Fibrillation", *Pace*, 9, (1986), pp. 1147-1153.

Buhr, Trina A., et al., "Novel Pacemaker Algorithm Diminishes Short-Coupled Ventricular Beats In Atrial Fibrillation", *Pace*, vol. 24, Part II, (Apr. 2001), 729.

Lau, Chu-Pak, et al., "Efficacy of Ventricular Rate Stabilization by Right Ventricular Pacing During Atrial Fibrillation", *Pace*, vol. 21 (Mar. 1998), 542-548.

Wittkampf, Fred H., et al., "Effect of Right Ventricular Pacing on Ventricular Rhythm During Atrial Fibrillation", *JACC*, vol. 11, No. 3, (Mar. 1988), 539-545.

"French CNH Equiptment Apporvals", *Clinica*, 417, p. 9, (Sep. 5, 1990), 3 pages.

"Rate-Adaptive Devices Impact Pacemaker Market", *Clinica*, 467, p. 16, (Sep. 11, 1991), 6 pages.

"Vitatron Medical Harmony Automatice Dual Chamber Pacemaker Product Information and Programming Guide", *Viatron Medical*, 22 p., (Date Unknown), Harmony Dual Chamber mentioned in publication Clinica, 467, p. 16, Sep. 11, 1991, "Rate Devices Impact Pacemaker Market", also mentioned in Clinica, 417, p. 9, Sep. 5, 1990 "French CNH Equiptment Approvals"., Product Brochure published by Vitatron Medical,22 pgs.

Blommaert, D., et al., "Effective Prevention of Atrial Fibrillation by Continuous Atrial Overdrive Pacing After Coronary Artery Bypass Surgery", *JACC*, vol. 35, No. 6, (May 2000), pp. 1411-1415.

Campbell, R.M., et al., "Atrial Overdrive Pacing for Conversion of Atrial Flutter in Children", *Pediatrics*, 75(4), (Apr. 1985), 730 - 736.

Garrigue, S., et al., "Prevention of Atrial Arrhythmias during DDD Pacing by Atrial Overdrive", *PACE*, vol. 21, (Sep. 1998),pp. 1751 - 1759.

Jenkins, et al., "Diagnosis of Atrial Fibrillation Using Electrogram from Chronic Leads: Evaluation of Computer Algorithm", *PACE*, 11, (1988),pp. 622-631.

Jung, J., et al., "Discrimination of Sinus Rhythm, Atrial Flutter, and Atrial Fibrillation Using Bipolar Endocardial Singnals", *Journal of Cardiovascular Electrophysiology*, 9 (7), (Jul. 1998), pp. 689-695.

Krig, David B., et al., Method and Apparatus for Treating Irregular Ventricular Contractions Such as During Atrial.

Arrhythmia, U.S. Appl. No. 09/316,515, Filed May 21, 6 pgs.

Krig, David B., et al., "Method and Apparatus for Treating Irregular Ventricular Contractions Such As During Atrial Arrhythmia", U.S. Appl. No. 10/643,590, Filed Aug. 19, 2003, 45 pgs.

Krig, David B., et al., "Method and Apparatus for Treating Irregular Ventricular Contraction Such as During Atrial Arrhythmia", U.S. Appl. No. 10/852,602, filed on May 24, 2004, 60 pgs.

Morris, et al., "Intracardiac Electrogram Transformation: Morphometric Implications for Implantable Devices", *Journal of Electrocardiology*, 29 Supplement, (1996),pp. 124-129.

Murgatroyd, F.D., et al., "A New Pacing Algorithm for Overdrive Suppression of Atrial Fibrillation", *Pace*, vol. 17., (Nov. 1994, Part), pp. 1966 - 1973.

Rodenhiser, Kristen, et al., "Method and Apparatus for Reducing Early Recurrence of Atrial Fibrillation with Defibrillation Shock Therapy", U.S. Ser. No. 09/570645, filed May 15, 2000, 10 pgs.

Schuller, et al., "Far Field R-Wave Sensing —an Old Problem Repeating", *PACE*, 19, Part II, NASPE Abstract No. 264,(1996),p. 631.

Stahmann, Jeffrey E., et al., "Apparatus and Method for Pacing Mode Switching During Atrial Tachyarrhythmias", U.S. Appl. No. 10/713,556, filed Nov. 13, 2003 26 pgs.

Stephany, et al., "Real-Time Estimation of Magnitude-Square Coherence for Use in Implantable Devices", *IEEE Computers in Cardiology*(1992),pp. 375-378.

Sutton, R., "Pacing in Atrial Arrhythmias", *PACE*, vol. 13, (Dec. 1990, Part), pp. 1823 - 1827.

Swiryn, S., et al., "Detection of Atrial Fibrillation by Pacemakers and Antiarrhythmic Devices ", *Nonpharmacological Management of Atrial Fibrillation*, Chapter 21, Futura Publishing Co, Inc. Armonk, NY, (1997),pp. 309-318.

Zhu, D.W., "Electrophysiology, Pacing and Arrhythmia", *Clin. Cardiol.*, vol. 19 (Sep. 1996),pp. 737 - 742.

Clark, David M., et al., "Hemodynamic Effects of an Irregular Sequence of Ventricular Lengths During Atrial Fibrillation", *JACC*, Vol , No. 4, (Oct. 1997), 1039-1045.

Guidant, "CONTAK CD CRT-D 1823", *Physician's System Manual*, Cardiac Resynchronization Therapy Defibrillator, (2002), 1-176.

Guidant, "CONTAK Renewal Model H135", *System Guide*, (2003), 1-331.

Guidant, "Contak TR CHFD Model 1241", *System Guide*, Congestive Heart Failure Device, (1999), 1-191.

Hsia, Peng W., et al., "Improved Nonthoractomy Defibrillation Based on Ventricular Fibrillation Waveform Characteristic", *PACE*, 18 —NASPE Abstracts, Abstract No. 29, (Apr. 1995), p. 803.

Hsu, William, et al., "Effect of Shock Timing on Defibrillation Success", *Pace*, 20, Part II, (1997), pp. 153-157.

Medtronic, "INSYNC Device Model 8040", *Device Reference Guide*, (Aug. 2001), 1-276.

Medtronic, "INSYNC ICD 7272", *System Reference Guide*, Dual chamber implantable cardioverter defibrillator with cardiac resynchronization therapy. A guide to the operation and programming of the 7272 InSync ICD Dual Chamber ImpLantable Cardioverter Defibrillator, (Jun. 2002), 1-367.

Medtronic, "INSYNC III Device Model 8042", *Device Programming Guide*, INSYNCE III Device Model 8042, Vision Programmer Software Model 9981, (2000), 1-260.

Medtronic, "INSYNC III Device Model 8042", *Device Reference Guide*, INSYNCE III Device Model 8042, Vision Programmer Software Model 9981, (2002), 1-252.

Medtronic, "INSYNC Marquis 7277", *Reference Manual*, Dual Chamber Implantable Cardioverter Defibrillator, (Mar. 2003), 1-435.

Medtronic, "INSYNC Model 8040 Device Programming Guide", *Device Programming Guide*, Device Model 8040 & Programmer Software Model 9980, (2001), 1-204.

St. Jude Medical, "Atlas +HF Models V-343, V-341", *User's Manual*, Implantable Cardioverter-Defibrillator, (Sep. 2003), 1-30.

St. Jude Medical, "Epic HF Model V-339", *User's Manual*, Implantable Cardioverter-Defibrillator, (Jul. 2002) 1-26.

St. Jude Medical, "Model 3510 Programmer with Model 3307 Software", *Reference Manual*, for Atlas, Atlas+, Epic, Epic +, Photon u and Photon Implantable Cardioverter/Defibrillators, (Sep. 2003), 1-314.

\* cited by examiner

CARDIAC RHYTHM MANAGEMENT SYSTEM WITH ATRIAL SHOCK TIMING OPTIMIZATION

CROSS REFERENCE TO RELATED APPLICATIONS

This application is a continuation of U.S. patent application Ser. No. 09/316,741, filed on May 21, 1999, now U.S. Pat. No. 6,430,438, the specification of which is herein incorporated by reference.

This application is also related to the following commonly assigned patent applications: U.S. patent application Ser. No. 09/837,019, filed on Apr. 18, 2001, now issued as U.S. Pat. No. 6,411,848; U.S. patent application Ser. No. 09/693,402, filed on Oct. 20, 2000, now issued as U.S. Pat. No. 6,353,759; U.S. patent application Ser. No. 09/316,515, filed on May 21, 1999, entitled "Method and Apparatus for Treating Irregular Ventricular Contractions Such as During Atrial Arrhythmia;" U.S. patent application Ser. No. 09/316,682, filed on May 21, 1999, now issued as U.S. Pat. No. 6351,669; and U.S. patent application Ser. No. 09/316,588, filed on May 21, 1999, now issued as U.S. Pat. No. 6,285,907, the specifications of which are herein incorporated by reference.

TECHNICAL FIELD

This invention relates generally to cardiac rhythm management systems and particularly, but not by way of limitation, to a cardiac rhythm management system with atrial shock timing optimization.

BACKGROUND

When functioning properly, the human heart maintains its own intrinsic rhythm, and is capable of pumping adequate blood throughout the body's circulatory system. However, some people have irregular cardiac rhythms, referred to as cardiac arrhythmias. Such arrhythmias result in diminished blood circulation. One mode of treating cardiac arrhythmias uses drug therapy. Drugs are often effective at restoring normal heart rhythms. However, drug therapy is not always effective for treating arrhythmias of certain patients. For such patients, an alternative mode of treatment is needed. One such alternative mode of treatment includes the use of a cardiac rhythm management system. Such systems are often implanted in the patient and deliver therapy to the heart.

Cardiac rhythm management systems include, among other things, pacemakers, also referred to as pacers. Pacers deliver timed sequences of low energy electrical stimuli, called pace pulses, to the heart, such as via a transvenous leadwire or catheter (referred to as a "lead") having one or more electrodes disposed in or about the heart. Heart contractions are initiated in response to such pace pulses (this is referred to as "capturing" the heart). By properly timing the delivery of pace pulses, the heart can be induced to contract in proper rhythm, greatly improving its efficiency as a pump. Pacers are often used to treat patients with bradyarrhythmias, that is, hearts that beat too slowly, or irregularly.

Cardiac rhythm management systems also include cardioverters or defibrillators that are capable of delivering higher energy electrical stimuli to the heart. Defibrillators are often used to treat patients with tachyarrhythmias, that is, hearts that beat too quickly. Such too-fast heart rhythms also cause diminished blood circulation because the heart isn't allowed sufficient time to fill with blood before contracting to expel the blood. Such pumping by the heart is inefficient. A defibrillator is capable of delivering an high energy electrical stimulus that is sometimes referred to as a defibrillation countershock. The countershock interrupts the tachyarrhythmia, allowing the heart to reestablish a normal rhythm for the efficient pumping of blood. In addition to pacers, cardiac rhythm management systems also include, among other things, pacer/defibrillators that combine the functions of pacers and defibrillators, drug delivery devices, and any other systems or devices for diagnosing or treating cardiac arrhythmias.

One problem faced by cardiac rhythm management systems is the proper treatment of atrial tachyarrhythmias, such as atrial fibrillation. Atrial fibrillation is a common cardiac arrhythmia which reduces the pumping efficiency of the heart, though not to as great a degree as in ventricular fibrillation. However, this reduced pumping efficiency requires the ventricle to work harder, which is particularly undesirable in sick patients that cannot tolerate additional stresses. As a result of atrial fibrillation, patients must typically limit their activity and exercise.

Although atrial fibrillation, by itself, is usually not life-threatening, prolonged atrial fibrillation may be associated with strokes, which are thought to be caused by blood clots forming in areas of stagnant blood flow. Treating such blood clots requires the use of anticoagulants. Atrial fibrillation may also cause pain, dizziness, and other irritation to the patient.

An even more serious problem, however, is the risk that atrial fibrillation may induce irregular ventricular heart rhythms by processes that are yet to be fully understood. Moreover, treatment of atrial fibrillation may also induce irregular ventricular heart rhythms. Such induced ventricular arrhythmias compromise pumping efficiency even more drastically than atrial arrhythmias and, in some instances, may be life-threatening. For these and other reasons, there is a need for safe and more effective treatment of atrial fibrillation that avoids inducing ventricular arrhythmias.

SUMMARY

The present cardiac rhythm management system provides, among other things, atrial shock timing optimization. The system detects an atrial tachyarrhythmia, such as atrial fibrillation. Such atrial tachyarrhythmias typically cause significant variability in the ventricular heart rate. The present system avoids delivering atrial cardioversion/defibrillation therapy during such irregular ventricular heart activity, because such conditions may be potentially proarrhythmic, such that delivering atrial cardioversion/defibrillation therapy could result in dangerous ventricular arrhythmias. Using Ventricular Rate Regularization ("VRR") techniques described below, the system stabilizes the ventricular heart rate to obtain less potentially proarrhythmic conditions for delivering the atrial tachyarrhythmia therapy. The system withholds delivery of atrial cardioversion/defibrillation therapy until the intervals between ventricular beats ("V—V intervals") meet certain criteria that decrease the chance that the atrial cardioversion/defibrillation therapy will induce a ventricular arrhythmia.

In one embodiment, the system includes a first method. The first method includes: (a) detecting an atrial tachyarrhythmia, (b) stabilizing a ventricular heart rate at a variable indicated rate based on an underlying intrinsic ventricular heart rate, (c) determining if potentially proarrhythmic conditions exist based on V—V intervals between ventricular events, and (d) delivering cardioversion/defibrillation therapy to the atrium if step (c) indicates no potentially proarrhythmic conditions exist, otherwise withholding the delivery of cardioversion/defibrillation therapy to the atrium until conditions become less potentially proarrhythmic.

In another embodiment, the system includes a second method. The second method includes: (a) obtaining V—V intervals between ventricular beats, (b) computing a first indicated pacing interval based on at least a most recent V—V interval duration and a previous value of the first indicated pacing interval, (c) providing pacing therapy, based on the first indicated pacing interval, (d) detecting a tachyarrhythmia in an atrium, and (e) delivering cardioversion/defibrillation therapy to the atrium.

In another embodiment, the system includes a cardiac rhythm management device. The device includes an atrial heart sensing circuit, a ventricular heart sensing circuit, a ventricular pacing therapy circuit, an atrial cardioversion/defibrillation therapy circuit, and a controller. The controller includes a ventricular rate stabilization module that stabilizes a ventricular heart rate at a variable indicated rate based on an underlying intrinsic ventricular heart rate. The controller also includes an atrial cardioversion/defibrillation control module that (a) determines if potentially proarrhythmic conditions exist based on V—V intervals between ventricular events, and (b) delivers cardioversion/defibrillation therapy to the atrium if conditions become less potentially proarrhythmic, and otherwise withholds the delivery of cardioversion/defibrillation therapy to the atrium. Other aspects of the invention will be apparent on reading the following detailed description of the invention and viewing the drawings that form a part thereof.

BRIEF DESCRIPTION OF THE DRAWINGS

In the drawings, like numerals describe substantially similar components throughout the several views. Like numerals having different letter suffixes represent different instances of substantially similar components.

DETAILED DESCRIPTION

Figure 1:
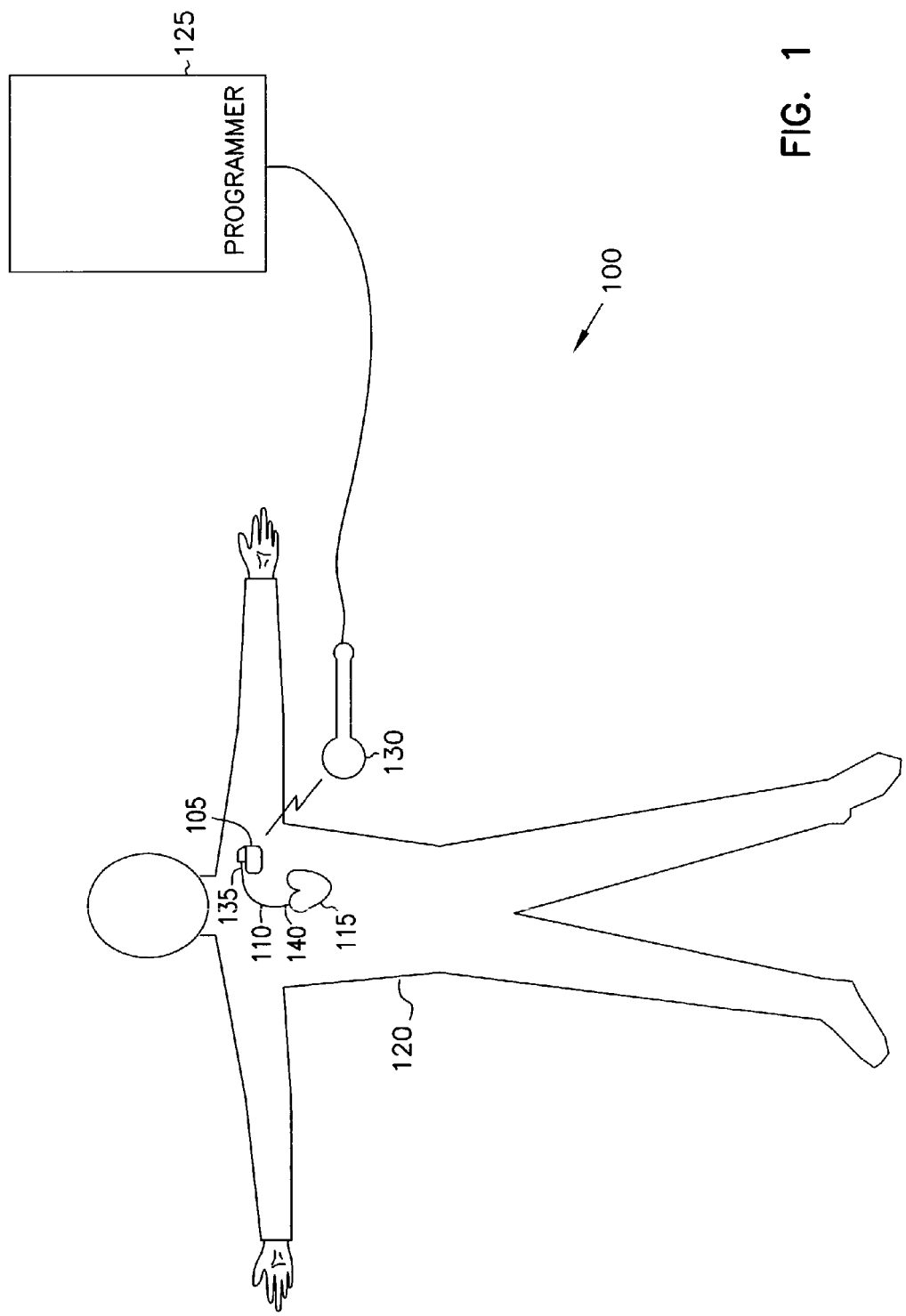
FIG. 1 is a schematic drawing illustrating one embodiment of portions of a cardiac rhythm management system and an environment in which it is used.

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the spirit and scope of the present invention. The following detailed description is, therefore, not to be taken in a limiting sense, and the scope of the present invention is defined by the appended claims and their equivalents. In the drawings, like numerals describe substantially similar components throughout the several views. Like numerals having different letter suffixes represent different instances of substantially similar components.

General Overview

This document describes, among other things, a cardiac rhythm management system with atrial shock timing optimization. The system detects an atrial tachyarrhythmia, such as atrial fibrillation. Such atrial tachyarrhythmias typically cause significant variability in the ventricular heart rate. The present system avoids delivering atrial cardioversion/defibrillation therapy during such irregular ventricular heart activity, because such conditions may be potentially proarrhythmic, such that delivering atrial cardioversion/defibrillation therapy could result in dangerous ventricular arrhythmias. Using Ventricular Rate Regularization ("VRR") techniques described below, the system stabilizes the ventricular heart rate to obtain less potentially proarrhythmic conditions for delivering the atrial tachyarrhythmia therapy. The system withholds delivery of atrial cardioversion/defibrillation therapy until the intervals between ventricular beats ("V—V intervals") meet certain criteria that decrease the chance that the atrial cardioversion/defibrillation therapy will induce a ventricular arrhythmia.

VENTRICULAR RATE REGULARIZATION (VRR) EXAMPLE

One aspect of the present system includes actively stabilizing the ventricular heart rate to obtain less potentially proarrhythmic conditions for delivering the atrial tachyarrhythmia therapy. One suitable technique for stabilizing ventricular heart rate is referred to as Ventricular Rate Regularization ("VRR"), described in Krig et al., U.S. patent application Ser. No. 09/316,515, filed on May 21, 1999, entitled "Method and Apparatus For Treating Irregular Ventricular Contractions Such As During Atrial Arrhythmia," and assigned to the assignee of the present patent application, and which is herein incorporated by reference in its entirety.

General System Overview and Examples

FIG. 1 is a schematic drawing illustrating, by way of example, but not by way of limitation, one embodiment of portions of a cardiac rhythm management system 100 and an environment in which it is used. In FIG. 1, system 100 includes an implantable cardiac rhythm management device 105, also referred to as an electronics unit, which is coupled by an intravascular endocardial lead 110, or other lead, to a heart 115 of patient 120. System 100 also includes an external programmer 125 providing wireless communication with device 105 using a telemetry device 130. Catheter lead 110 includes a proximal end 135, which is coupled to device 105, and a distal end 140, which is coupled to one or more portions of heart 115.

Figure 2:
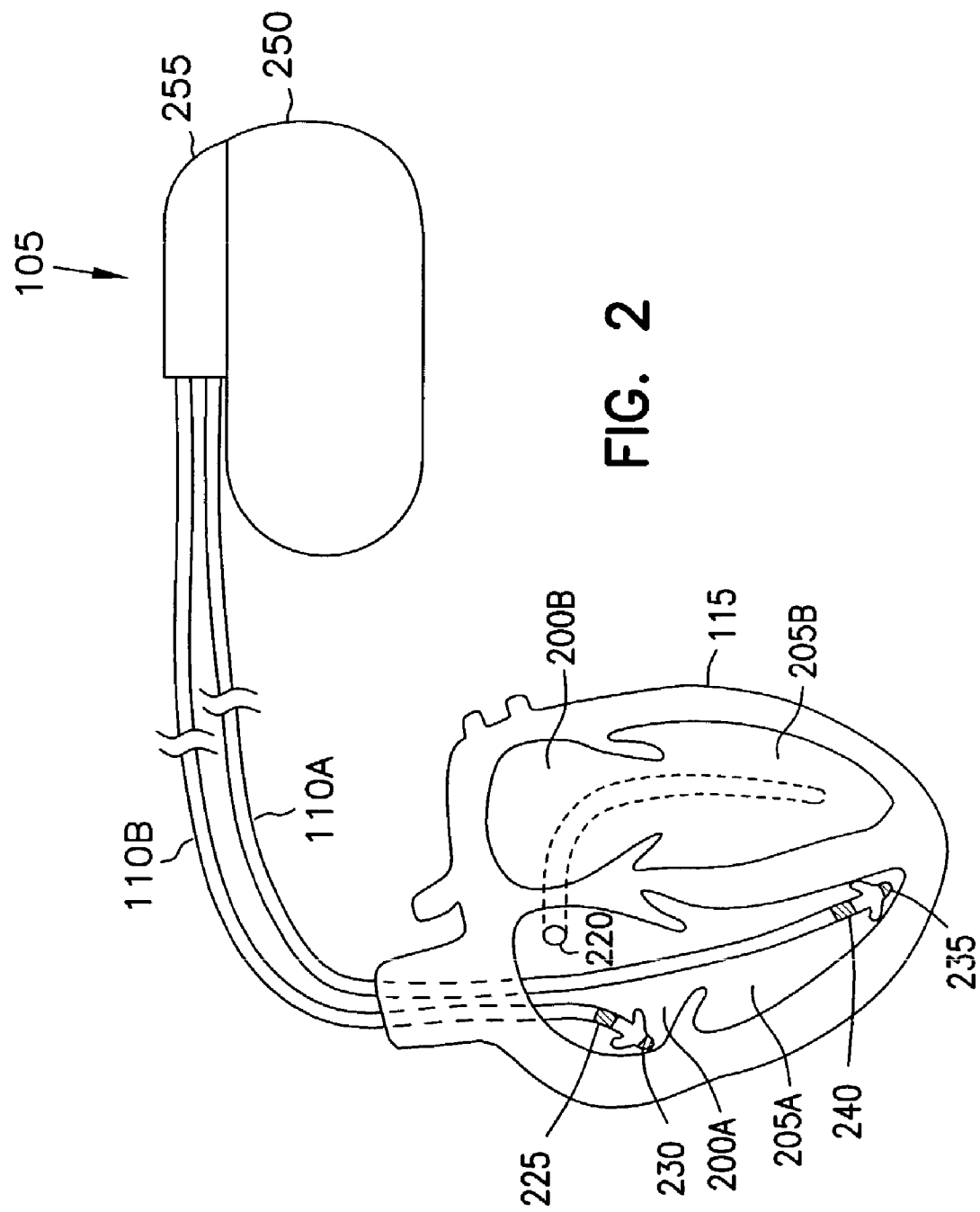
FIG. 2 is a schematic drawing illustrating one embodiment of a cardiac rhythm management device coupled by leads to portions of a heart.

FIG. 2 is a schematic drawing illustrating, by way of example, but not by way of limitation, one embodiment of device 105 coupled by leads 110A–B to heart 115, which includes a right atrium 200A, a left atrium 200B, a right ventricle 205A, a left ventricle 205B, and a coronary sinus 220 extending from right atrium 200A. In this embodiment, atrial lead 110A includes electrodes (electrical contacts) disposed in, around, or near an atrium 200 of heart 115, such as ring electrode 225 and tip electrode 230, for sensing signals and/or delivering pacing therapy to the atrium 200. Lead 110A optionally also includes additional electrodes, such as for delivering atrial and/or ventricular cardioversion/defibrillation and/or pacing therapy to heart 115.

In FIG. 2, a ventricular lead 110B includes one or more electrodes, such as tip electrode 235 and ring electrode 240, for delivering sensing signals and/or delivering pacing therapy. Lead 110B optionally also includes additional electrodes, such as for delivering atrial and/or ventricular cardioversion/defibrillation and/or pacing therapy to heart 115. Device 105 includes components that are enclosed in a hermetically-sealed can 250. Additional electrodes may be located on the can 250, or on an insulating header 255, or on other portions of device 105, for providing unipolar pacing and/or defibrillation energy in conjunction with the electrodes disposed on or around heart 115. Other forms of electrodes include meshes and patches which may be applied to portions of heart 115 or which may be implanted in other areas of the body to help "steer" electrical currents produced by device 105. The present method and apparatus will work in a variety of configurations and with a variety of electrical contacts or "electrodes."

Example Cardiac Rhythm Management Device

Figure 3:
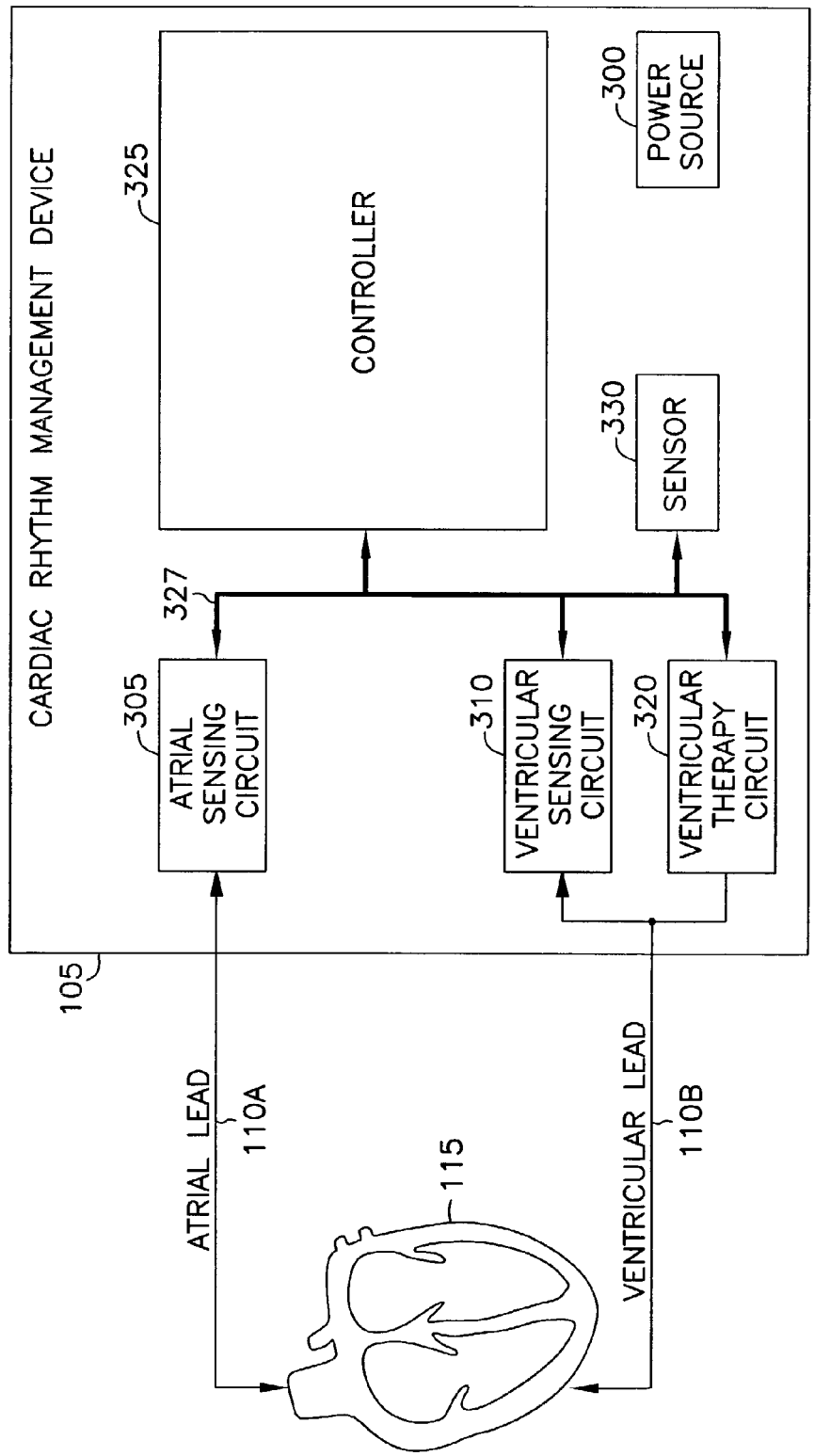
FIG. 3 is a schematic diagram illustrating generally one embodiment of portions of a cardiac rhythm management device which is coupled to a heart.

FIG. 3 is a schematic diagram illustrating generally, by way of example, but not by way of limitation, one embodiment of portions of device 105, which is coupled to heart 115. Device 105 includes a power source 300, an atrial sensing circuit 305, a ventricular sensing circuit 310, a ventricular therapy circuit 320, and a controller 325.

Atrial sensing circuit 305 is coupled by atrial lead 110A to heart 115 for receiving, sensing, and/or detecting electrical atrial heart signals. Such atrial heart signals include atrial activations (also referred to as atrial depolarizations or P-waves), which correspond to atrial contractions. Such atrial heart signals include normal atrial rhythms, and abnormal atrial rhythms including atrial tachyarrhythmias, such as atrial fibrillation, and other atrial activity. Atrial sensing circuit 305 provides one or more signals to controller 325, via node/bus 327, based on the received atrial heart signals. Such signals provided to controller 325 indicate, among other things, the presence of atrial fibrillation.

Ventricular sensing circuit 310 is coupled by ventricular lead 110B to heart 115 for receiving, sensing, and/or detecting electrical ventricular heart signals, such as ventricular activations (also referred to as ventricular depolarizations or R-waves), which correspond to ventricular contractions. Such ventricular heart signals include normal ventricular rhythms, and abnormal ventricular rhythms, including ventricular tachyarrhythmias, such as ventricular fibrillation, and other ventricular activity, such as irregular ventricular contractions resulting from conducted signals from atrial fibrillation. Ventricular sensing circuit 310 provides one or more signals to controller 325, via node/bus 327, based on the received ventricular heart signals. Such signals provided to controller 325 indicate, among other things, the presence of ventricular depolarizations, whether regular or irregular in rhythm.

Ventricular therapy circuit 320 provides ventricular pacing therapy, as appropriate, to electrodes located at or near one of the ventricles 205 of heart 115 for obtaining resulting evoked ventricular depolarizations. In one embodiment, ventricular therapy circuit 320 also provides cardioversion/defibrillation therapy, as appropriate, to electrodes located at or near one of the ventricles 205 of heart 115, for terminating ventricular fibrillation and/or other ventricular tachyarrhythmias.

Controller 325 controls the delivery of therapy by ventricular therapy circuit 320 and/or other circuits, based on heart activity signals received from atrial sensing circuit 305 and ventricular sensing circuit 310, as discussed below. Controller 325 includes various modules, which are implemented either in hardware or as one or more sequences of steps carried out on a microprocessor or other controller. Such modules are illustrated separately for conceptual clarity; it is understood that the various modules of controller 325 need not be separately embodied, but may be combined and/or otherwise implemented, such as in software/firmware.

In general terms, sensing circuits 305 and 310 sense electrical signals from heart tissue in contact with the catheter leads 110A–B to which these sensing circuits 305 and 310 are coupled. Sensing circuits 305 and 310 and/or controller 325 process these sensed signals. Based on these sensed signals, controller 325 issues control signals to therapy circuits, such as ventricular therapy circuit 320, if necessary, for the delivery of electrical energy (e.g., pacing and/or defibrillation pulses) to the appropriate electrodes of leads 110A–B. Controller 325 may include a microprocessor or other controller for execution of software and/or firmware instructions. The software of controller 325 may be modified (e.g., by remote external programmer 105) to provide different parameters, modes, and/or functions for the implantable device 105 or to adapt or improve performance of device 105.

In one further embodiment, one or more sensors, such as sensor 330, may serve as inputs to controller 325 for adjusting the rate at which pacing or other therapy is delivered to heart 115. One such sensor 330 includes an accelerometer that provides an input to controller 325 indicating increases and decreases in physical activity, for which controller 325 increases and decreases pacing rate, respectively. Another such sensor includes an impedance measurement, obtained from body electrodes, which provides an indication of increases and decreases in the patient's respiration, for example, for which controller 325 increases and decreases pacing rate, respectively. Any other sensor 330 providing an indicated pacing rate can be used.

Figure 4:
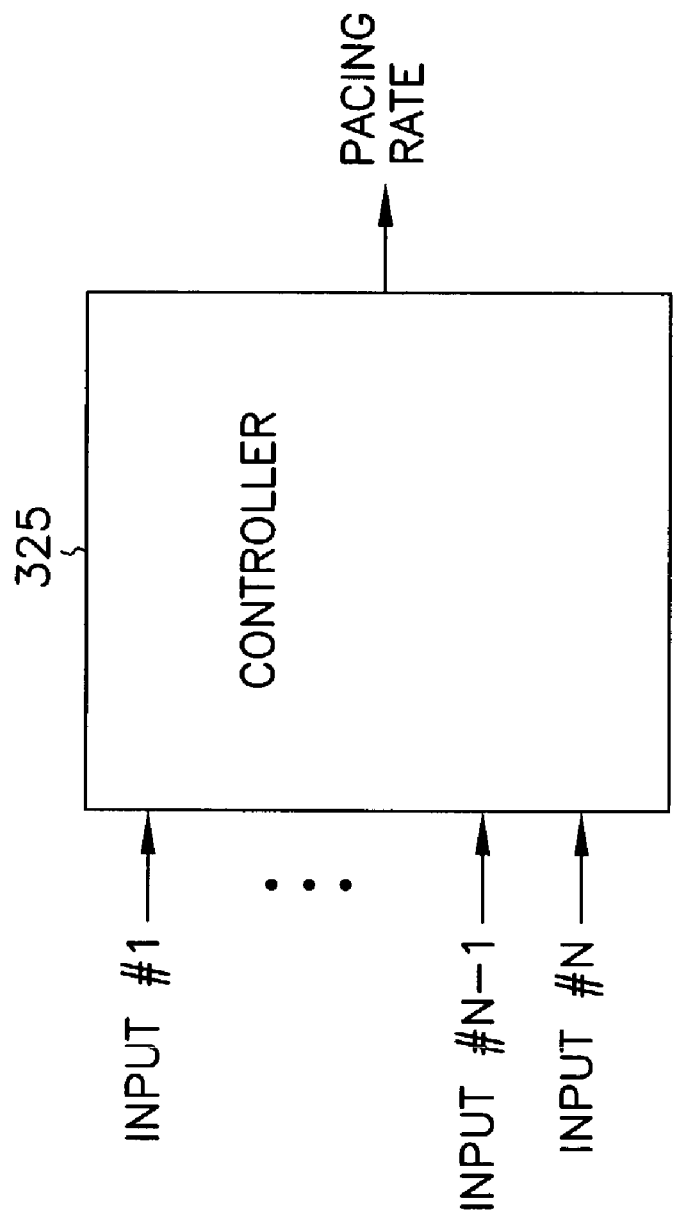
FIG. 4 is a schematic diagram illustrating generally one embodiment of a controller that includes several different inputs to modify the rate at which pacing or other therapy is delivered.

FIG. 4 is a schematic diagram illustrating generally, by way of example, but not by way of limitation, one embodiment of controller 325 that includes several different inputs to modify the rate at which pacing or other therapy is delivered. For example, Input #1 may provide information about left ventricular rate, Input #2 may provide an accelerometer-based indication of activity, and Input #3 may provide an impedance-based indication of respiration, such as minute ventilation. Based on at least one of these and/or other inputs, controller 325 provides an output indication of pacing rate as a control signal delivered to a therapy circuit, such as to ventricular therapy circuit 320. Ventricular therapy circuit 320 issues pacing pulses based on one or more such control signals received from controller 325. Control of the pacing rate may be performed by controller 325, either alone or in combination with peripheral circuits or modules, using software, hardware, firmware, or any combination of the like. The software embodiments provide flexibility in how inputs are processed and may also provide the opportunity to remotely upgrade the device software while still implanted in the patient without having to perform surgery to remove and/or replace the device 105.

Controller Example 1

Figure 5:
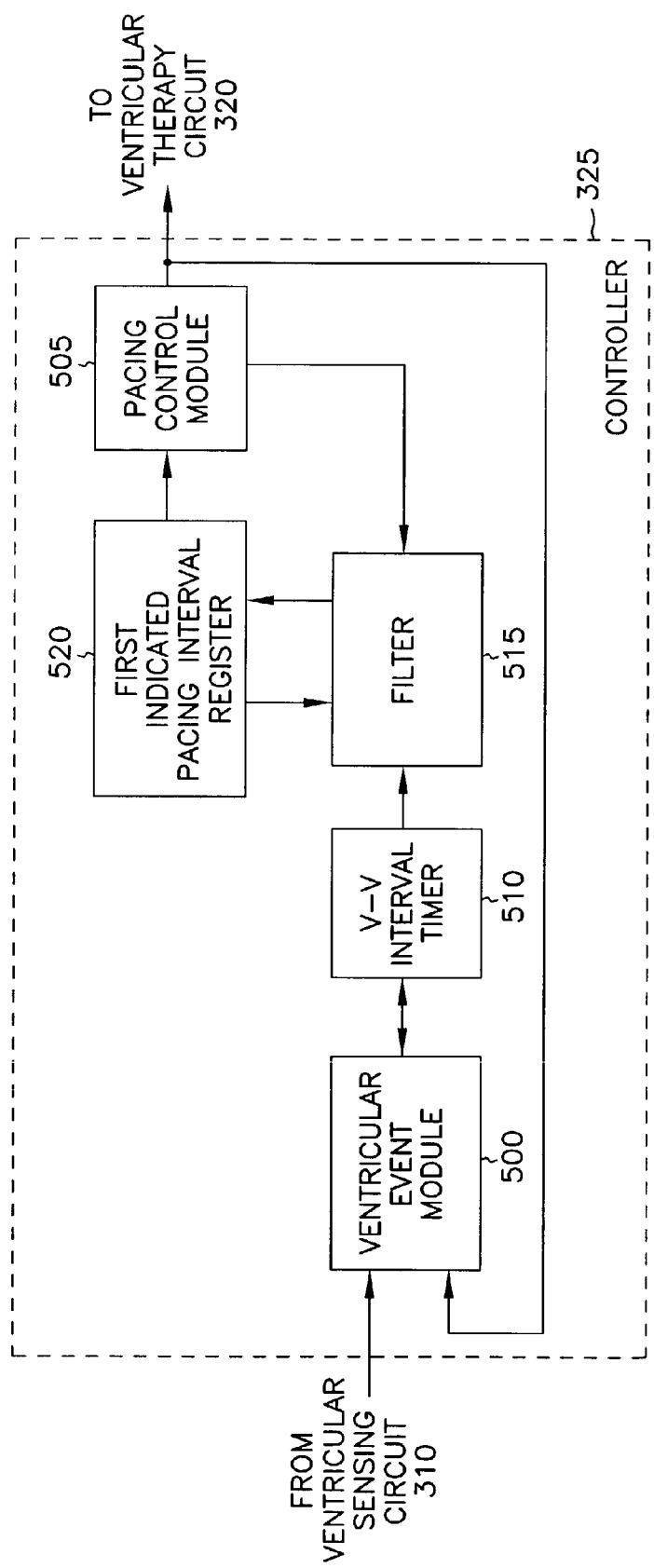
FIG. 5 is a schematic diagram illustrating generally one conceptualization of portions of a controller.

FIG. 5 is a schematic diagram illustrating generally, by way of example, but not by way of limitation, one conceptualization of portions of controller 325. At least one signal from ventricular sensing circuit 310 is received by ventricular event module 500, which recognizes the occurrence of ventricular events included within the signal. Such events are also referred to as "beats," "activations," "depolarizations," "QRS complexes," "R-waves," "contractions." Ventricular event module 500 detects intrinsic events (also referred to as sensed events) from the signal obtained from ventricular sensing circuit 310. Ventricular event module 500 also detects evoked events (resulting from a pace) either from the signal obtained from ventricular sensing circuit 310, or preferably from a ventricular pacing control signal obtained from pacing control module 505, which also triggers the delivery of a pacing stimulus by ventricular therapy circuit 320. Thus, ventricular events include both intrinsic/sensed events and evoked/paced events.

A time interval between successive ventricular events, referred to as a V—V interval, is recorded by a first timer, such as V—V interval timer 510. A filter 515 computes a "first indicated pacing interval," i.e., one indication of a desired time interval between ventricular events or, stated differently, a desired ventricular heart rate. The first indicated pacing interval is also referred to as a ventricular rate regularization (VRR) indicated pacing interval. In various embodiments, filter 515 includes an averager, a weighted averager, a median filter, an infinite impulse response (IIR) filter, a finite impulse response (FIR) filter, or any other analog or digital signal processing circuit providing the desired signal processing described more particularly below.

In one embodiment, filter 515 computes a new value of the first indicated pacing interval based on the duration of the most recent V—V interval recorded by timer 510 and on a previous value of the first indicated pacing interval stored in first indicated pacing interval register 520. Register 520 is then updated by storing the newly computed first indicated pacing interval in register 520. Based on the first indicated pacing interval stored in register 520, pacing control module 505 delivers control signals to ventricular therapy circuit 320 for delivering therapy, such as pacing stimuli, at the VRR-indicated ventricular heart rate corresponding to the inverse of the duration of the first indicated pacing interval.

Filter Example 1

In general terms, for one embodiment, device 105 obtains V—V intervals between successive sensed or evoked ventricular beats. Device 105 computes a new first indicated pacing interval based at least in part on the duration of the most recent V—V interval and a previous value of the first indicated pacing interval. Device 105 provides pacing therapy delivered at a rate corresponding to the inverse of the duration of the first indicated pacing interval.

Figure 6:
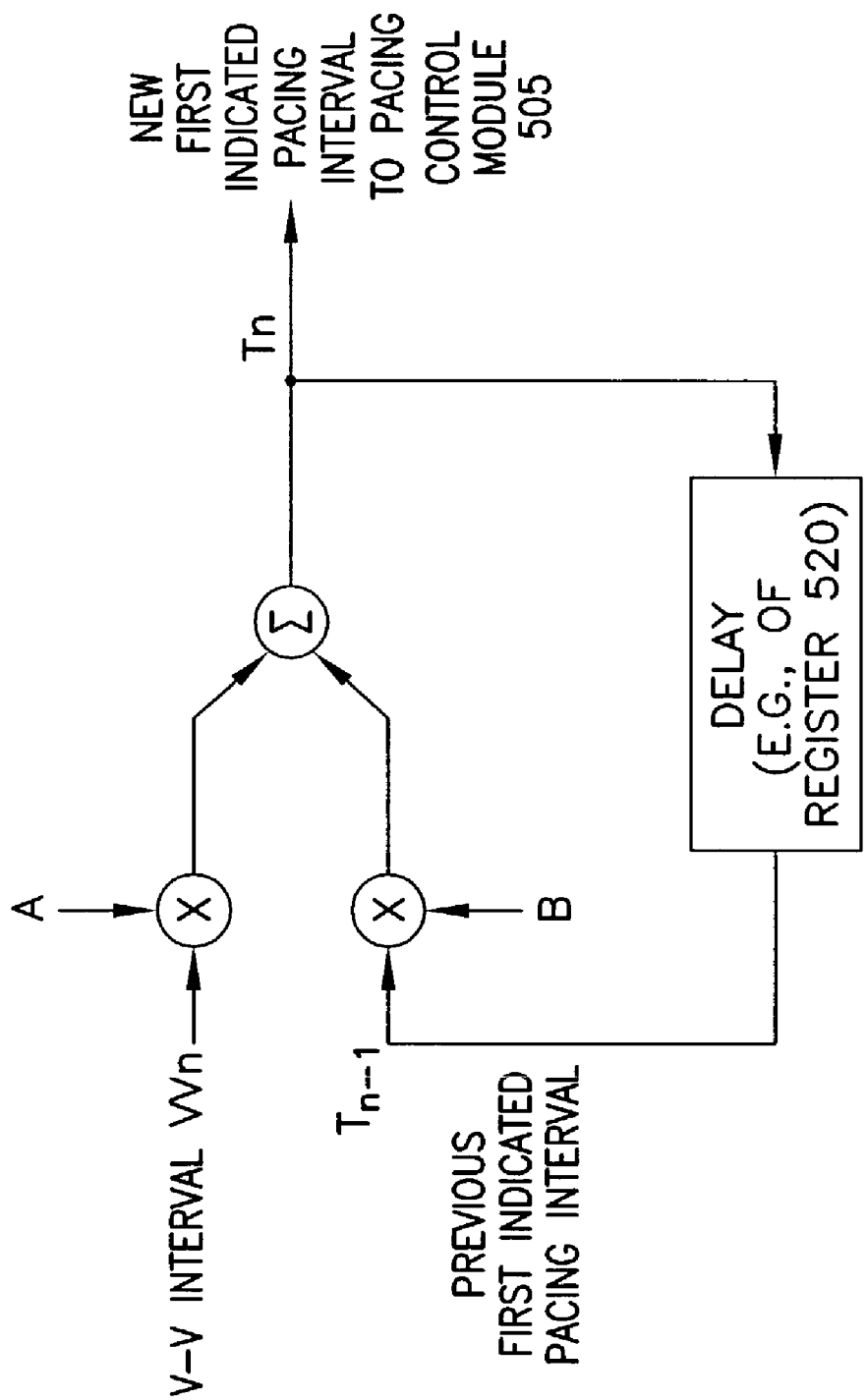
FIG. 6 is a signal flow diagram illustrating generally one embodiment of operating a filter.

FIG. 6 is a signal flow diagram illustrating generally, by way of example, but not by way of limitation, one embodiment of operating filter 515. Upon the occurrence of a sensed or evoked ventricular beat, timer 510 provides filter 515 with the duration of the V—V interval concluded by that beat, which is referred to as the most recent V—V interval ($VV_n$). Filter 515 also receives the previous value of the first indicated pacing interval ($T_{n-1}$) stored in register 520. The most recent V—V interval $VV_n$ and the previous value of the first indicated pacing interval $T_{n-1}$ are each scaled by respective constants A and B, and then summed to obtain a new value of the first indicated pacing interval ($T_n$), which is stored in register 520 and provided to pacing control module 505. In one embodiment, the coefficients A and B are different values, and are either programmable, variable, or constant.

If no ventricular beat is sensed during the new first indicated pacing interval $T_n$, which is measured as the time from the occurrence of the ventricular beat concluding the most recent V—V interval $VV_n$, then pacing control module 505 instructs ventricular therapy circuit 320 to deliver a ventricular pacing pulse upon the expiration of the new first indicated pacing interval $T_n$. In one embodiment, operation of the filter is described by $T_n = A \cdot VV_n + B \cdot T_{n-1}$, where A and B are coefficients (also referred to as "weights"), $VV_n$, is the most recent V—V interval duration, and $T_{n-1}$ is the previous value of the first indicated pacing interval.

Initialization of filter 515 includes seeding the filter by storing, in register 520, an initial interval value. In one embodiment, register 520 is initialized to an interval value corresponding to a lower rate limit (LRL), i.e., a minimum rate at which pacing pulses are delivered by device 105. Register 520 could alternatively be initialized with any other suitable value.

Filter Example 2

In one embodiment, operation of filter 515 is based on whether the beat concluding the most recent V—V interval $VV_n$, is a sensed/intrinsic beat or a paced/evoked beat. In this embodiment, the pacing control module 505, which controls the timing and delivery of pacing pulses, provides an input to filter 515 that indicates whether the most recent V—V interval $VV_n$ was concluded by an evoked beat initiated by a pacing stimulus delivered by device 105, or was concluded by an intrinsic beat sensed by ventricular sensing circuit 310.

In general terms, if the most recent V—V interval $VV_n$, is concluded by a sensed/intrinsic beat, then filter 515 provides a new first indicated pacing interval $T_n$ that is adjusted from the value of the previous first indicated pacing interval $T_{n-1}$ such as, for example, decreased by an amount that is based at least partially on the duration of the most recent V—V interval $VV_n$, and on the duration of the previous value of the first indicated pacing interval $T_{n-1}$. If, however, the most recent V—V interval VVn is concluded by a paced/evoked beat, then filter 515 provides a new first indicated pacing interval $T_n$ that is increased from the value of the previous first indicated pacing interval $T_{n-1}$, such as, for example, by an amount that is based at least partially on the duration of the most recent V—V interval $VV_n$, and on the duration of the previous value of the first indicated pacing interval $T_{n-1}$. If no ventricular beat is sensed during the new first indicated pacing interval $T_n$, which is measured as the time from the occurrence of the ventricular beat concluding the most recent V—V interval $VV_n$, then pacing control module 505 instructs ventricular therapy circuit 320 to deliver a ventricular pacing pulse upon the expiration of the new first indicated pacing interval $T_n$.

Figure 7:
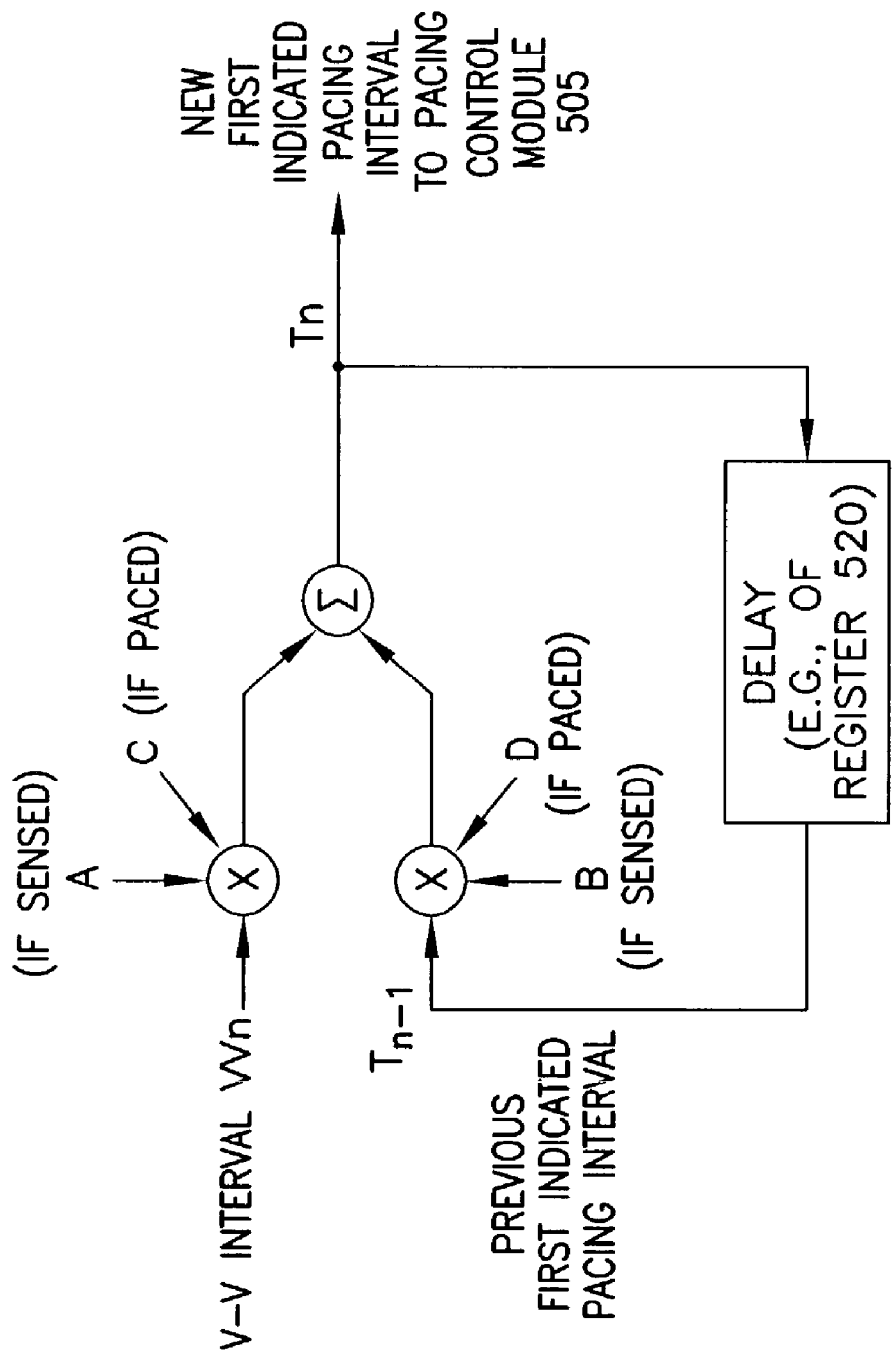
FIG. 7 is a signal flow diagram illustrating generally aspects of another conceptualization of operating the filter.

FIG. 7 is a signal flow diagram, illustrating generally, by way of example, but not by way of limitation, another conceptualization of operating filter 515, with certain differences from FIG. 6 more particularly described below. In this embodiment, the pacing control module 505, which controls the timing and delivery of pacing pulses, provides an input to filter 515 that indicates whether the most recent V—V interval $VV_n$ was concluded by an evoked beat initiated by a pacing stimulus delivered by device 105, or was concluded by an intrinsic beat sensed by ventricular sensing circuit 310.

If the most recent V—V interval $VV_n$ was concluded by an intrinsic beat, then the most recent V—V interval $VV_n$ and the previous value of the first indicated pacing interval $T_{n-1}$ are each scaled by respective constants A and B, and then summed to obtain the new value of the first indicated pacing interval $T_n$, which is stored in register 520 and provided to pacing control module 505. Alternatively, if the most recent V—V interval $VV_n$ was concluded by a evoked/paced beat, then the most recent V—V interval $VV_n$ and the previous value of the first indicated pacing interval $T_{n-1}$ are each scaled by respective constants C and D, and then summed to obtain the new value of the first indicated pacing interval $T_n$, which is stored in register 520 and provided to pacing control module 505. In one embodiment, the coefficients C and D are different from each other, and are either programmable, variable, or constant. In a further embodiment, the coefficient C is a different value from the coefficient A, and/or the coefficient D is a different value than the coefficient B, and these coefficients are either programmable, variable, or constant. In another embodiment, the coefficient D is the same value as the coefficient B.

In one embodiment, operation of filter 515 is described by $T_n = A \cdot VV_n + B \cdot T_{n-1}$, if $VV_n$ is concluded by an intrinsic beat, and is described by $T_n = C \cdot VV_n + D \cdot T_{n-1}$, if $VV_n$ is concluded by a paced beat, where A, B, C and D are coefficients (also referred to as "weights"), $VV_n$ is the most recent V—V interval duration, $T_n$ is the new value of the first indicated pacing interval, and $T_{n-1}$ is the previous value of the first indicated pacing interval. If no ventricular beat is sensed during the new first indicated pacing interval $T_n$, which is measured as the time from the occurrence of the ventricular beat concluding the most recent V—V interval $VV_n$, then pacing control module 505 instructs ventricular therapy circuit 320 to deliver a ventricular pacing pulse upon the expiration of the new first indicated pacing interval $T_n$.

Filter Example 3

Figure 8:
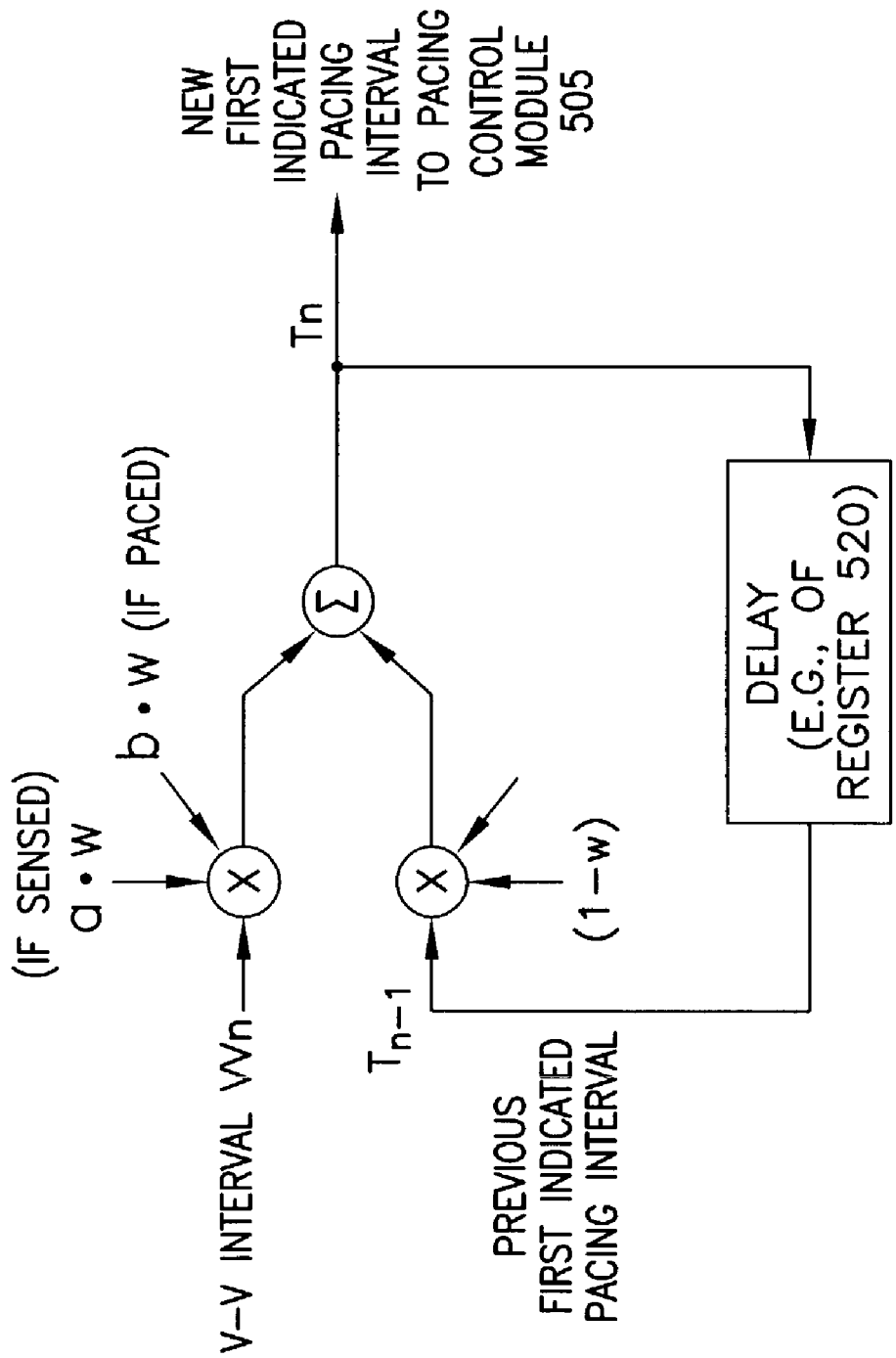
FIG. 8 is a signal flow diagram illustrating generally aspects of a further conceptualization of operating the filter.

In another embodiment, these coefficients can be, more Particularly described using an intrinsic coefficient (a), a paced coefficient (b), and a weighting coefficient (w). In one such embodiment, $A = a \cdot w$, $B = (1-w)$, $C = b \cdot w$, and $D = (1-w)$. In one example, operation of the filter 515 is described by $T_n = a \cdot w \cdot VV_n + (1-w) \cdot T_{n-1}$, if $VV_n$ is concluded by an intrinsic beat, otherwise is described by $T_n = b \cdot w \, VV_n + (1-w) \cdot T_{n-1}$, if $VV_n$ is concluded by a paced beat, as illustrated generally, by way of example, but not by way of limitation, in the signal flow graph of FIG. 8. If no ventricular beat is sensed during the new first indicated pacing interval $T_n$, which is measured as the time from the occurrence of the ventricular beat concluding the most recent V—V interval $VV_n$, then pacing control module 505 instructs ventricular therapy circuit 320 to deliver a ventricular pacing pulse upon the expiration of the new first indicated pacing interval $T_n$. In one embodiment, the coefficients a and b are different from each other, and are either programmable, variable, or constant.

The above-described parameters (e.g., A, B, C, D, a, b, w) are stated in terms of time intervals (e.g., $VV_n$, $T_n$, $T_{n-1}$). However, an alternate system may produce results in terms of rate, rather than time intervals, without departing from the present method and apparatus. In one embodiment, weighting coefficient w, intrinsic coefficient a, and paced coefficient b, are variables. Different selections of w, a, and b, will result in different operation of the present method and apparatus. For example, as w increases the weighting effect of the most recent V—V interval $VV_n$ increases and the weighting effect of the previous first indicated pacing rate $T_{n-1}$ decreases. In one embodiment, $w = \frac{1}{16} = 0.0625$. In another embodiment, $w = \frac{1}{32}$. Another possible range for w is from $w = \frac{1}{2}$ to $w = \frac{1}{1024}$. A further possible range for w is from $w \approx 0$ to $w \approx 1$. Other values of w, which need not include division by powers of two, may be substituted without departing from the present method and apparatus.

In one embodiment, intrinsic coefficient a, is selected to be greater than 0.5, or to be greater than 1.0. In one example, the intrinsic coefficient a is selected to be lesser in value than the pacing coefficient b. In one example, a≈1.1 and b≈1.2. In another embodiment a=0.9 and b=1.1. One possible range for a is from a=0.5 to a=2.0, and for b is from b=1.0 to b=3.0. The coefficients may vary without departing from the present method and apparatus.

In one embodiment, for b>1 and for substantially regular V—V intervals, filter 515 provides a new first indicated pacing interval $T_n$ that is at least slightly longer than the expected intrinsic V—V interval being measured by timer 515. Thus, if the intrinsic V—V interval being timed is consistent with the duration of previously received V—V intervals, then filter 515 avoids triggering a pacing stimulus. In such a case, a pacing pulse is delivered only if the presently timed V—V interval becomes longer than the previous substantially constant V—V intervals. In general terms, filter 515 operates so that pacing pulses are typically inhibited if the ventricular rate is substantially constant. However, if the measured V—V intervals become irregular, then filter 515 operates, over a period of one or several such V—V intervals, to shorten the first indicated pacing interval $T_n$ so that pacing stimuli are being delivered.

According to one aspect of the invention, it is believed that if the irregular V—V intervals are caused by a conducted atrial tachyarrhythmia, then pacing the ventricle will regularize the ventricular heart rate by establishing retrograde conduction from the ventricle. This, in turn, blocks forward conduction of atrial signals through the atrioventricular (A-V) node. As a result, irregular atrial signals do not trigger resulting irregular ventricular contractions. According to another aspect of the invention, however, this method and apparatus will not introduce pacing pulses until the heartbeat becomes irregular. Therefore, the heart is assured to pace at its intrinsic rate when regular ventricular contractions are sensed.

Controller Example 2

Figure 9:
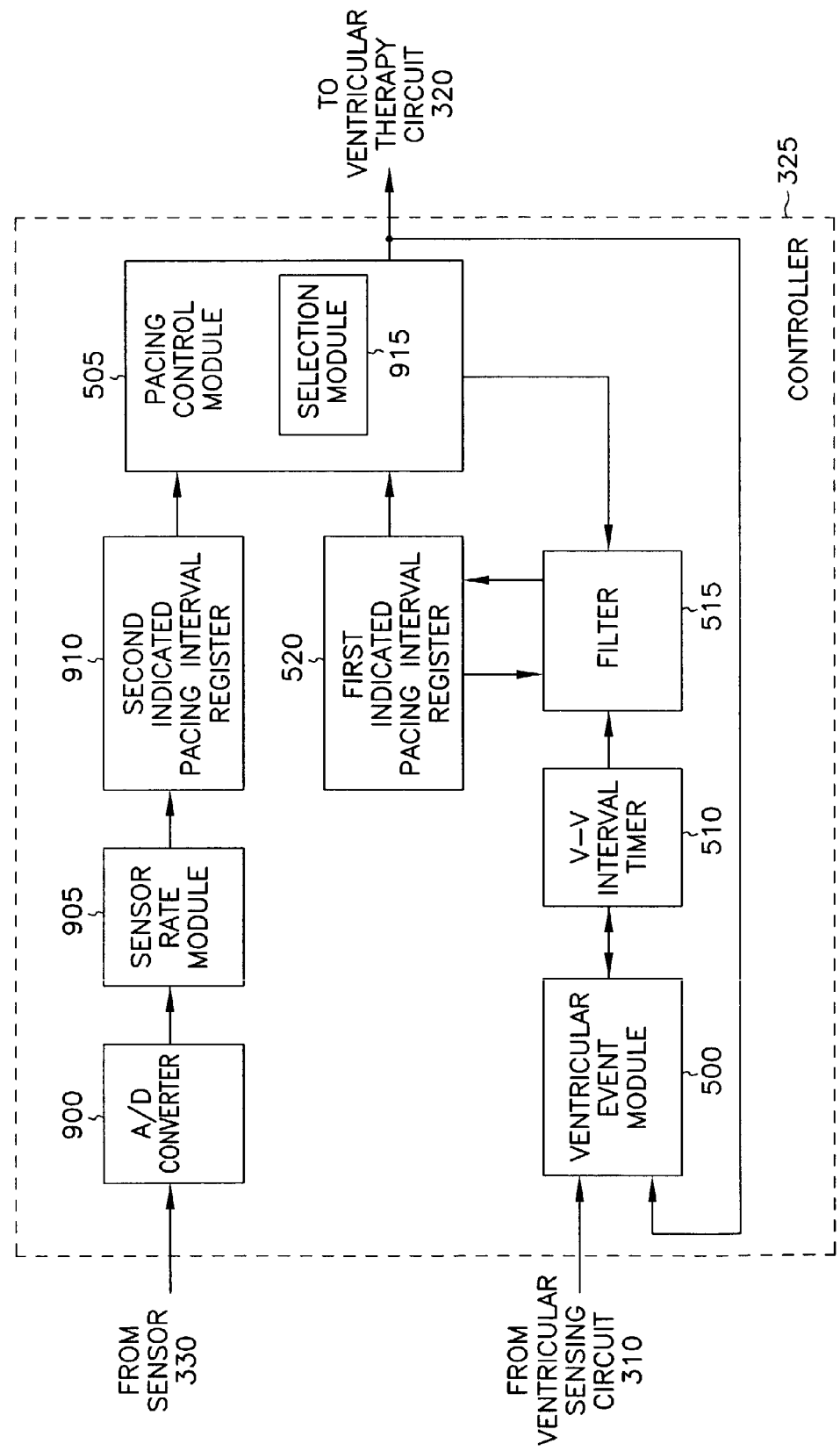
FIG. 9 is a schematic diagram illustrating generally another conceptualization of portions of a controller.

FIG. 9 is a schematic diagram illustrating generally, by way of example, but not by way of limitation, another conceptualization of portions of controller 325, with certain differences from FIG. 5 more particularly described below. In FIG. 9, controller 325 receives from sensor 330 a signal including information from which a physiologically desired heart rate (e.g., based on the patient's activity, respiration, or any other suitable indicator of metabolic need) can be derived. The sensor signal is digitized by an A/D converter 900. The digitized signal is processed by a sensor rate module 905, which computes a desired heart rate that is expressed in terms of a second indicated pacing interval stored in register 910.

Pacing control module 505 delivers a control signal, which directs ventricular therapy circuit 320 to deliver a pacing pulse, based on either (or both) of the first or second indicated pacing intervals, stored in registers 520 and 910, respectively, or both. In one embodiment, pacing control module 505 includes a selection module 915 that selects between the new first indicated pacing interval $T_n$ and the sensor-based second indicated pacing interval.

In one embodiment, selection module 915 selects the shorter of the first and second indicated pacing intervals as the selected indicated pacing interval $S_n$. If no ventricular beat is sensed during the selected indicated pacing interval $S_n$, which is measured as the time from the occurrence of the ventricular beat concluding the most recent V—V interval $VV_n$, then pacing control module 505 instructs ventricular therapy circuit 320 to deliver a ventricular pacing pulse upon the expiration of the selected indicated pacing interval $S_n$.

In general terms, for this embodiment, the ventricle is paced at the higher of the sensor indicated rate and the VRR indicated rate. If, for example, the patient is resting, such that the sensor indicated rate is lower than the patient's intrinsic rate, and the patient's intrinsic rate is substantially constant, then the intrinsic rate is higher than the VRR indicated rate. As a result, pacing pulses generally will not be delivered. But if, for example, the patient is resting, but with an atrial tachyarrhythmia that induces irregular ventricular contractions, then pacing pulses generally will be delivered at the VRR indicated rate. In another example, if the patient is active, such that the sensor indicated rate is higher than the VRR indicated rate, then pacing pulses generally will be delivered at the sensor indicated rate In an alternative embodiment, the pacing rate is determined by blending the sensor indicated rate and the VRR indicated rate, rather than by selecting the higher of these two indicated rates (i.e., the shorter of the first and second indicated pacing intervals).

In another embodiment, selection module 915 provides a selected indicated pacing interval $S_n$ based on a blending of both the first and second indicated pacing intervals. In one such example, selection module 915 applies predetermined or other weights to the first and second indicated pacing intervals to compute the selected pacing interval $S_n$.

Controller Example 2

Figure 10:
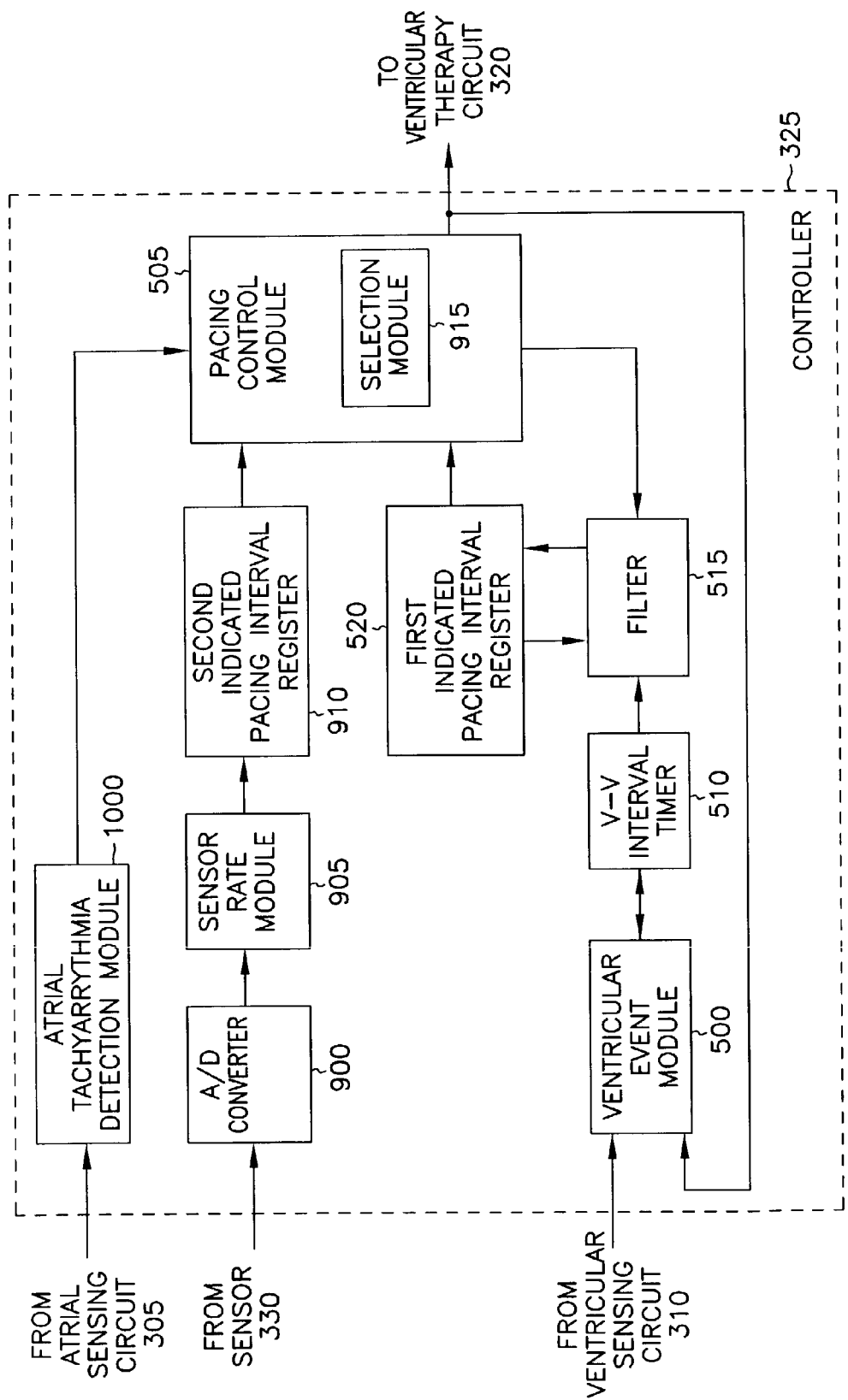
FIG. 10 is a schematic diagram illustrating generally a further conceptualization of portions of the controller.

FIG. 10 is a schematic diagram illustrating generally, by way of example, but not by way of limitation, another conceptualization of portions of controller 325, with certain differences from FIG. 9 more particularly described below. In FIG. 10, controller 325 includes an atrial tachyarrhythmia (AT) detection module 1000 that receives a signal from atrial sensing circuit 305. The received signal includes information about atrial events, from which AT detection module 1000 determines the presence or absence of one or more atrial tachyarrhythmias, such as atrial fibrillation.

In one embodiment, AT detection module 1000 provides a control signal, to pacing control module 505, that indicates the presence or absence of an atrial tachyarrhythmia, such as atrial fibrillation. In one embodiment, selection module 915 selects between the first and second indicated pacing intervals as illustrated, by way of example, but not by way of limitation, in Table 1.

TABLE 1

Example Selection Based on AT Detection, 1st Indicated Pacing Interval, and 2nd Indicated Pacing Interval

| AT Present? | 1st Indicated Pacing Interval < 2nd Indicated Pacing Interval? | 1st Indicated Pacing Interval ≧ 2nd Indicated Pacing Interval? |
|---|---|---|
| Yes, AT Present | $S_n \leftarrow$ 1st Indicated Pacing Interval (i.e., VRR) | $S_n \leftarrow$ 2nd Indicated Pacing Interval (e.g., Sensor) |
| No, AT not Present | $S_n \leftarrow$ 2nd Indicated Pacing Interval (e.g., Sensor) | $S_n \leftarrow$ 2nd Indicated Pacing Interval (e.g., Sensor) |

In this embodiment, if an atrial tachyarrhythmia is present and the first indicated pacing interval is shorter than the second indicated pacing interval, then selection module 915 selects the first indicated pacing interval, which is based on the VRR techniques described above, as the selected indicated pacing interval $S_n$. Otherwise, selection module 915 selects the second indicated pacing interval, which in one embodiment is based on the sensor indications, as the selected indicated pacing interval $S_n$. As discussed above, if no ventricular beat is sensed during the selected indicated pacing interval Snow which is measured as the time from the occurrence of the ventricular beat concluding the most recent V—V interval $VV_n$, then pacing control module 505 instructs ventricular therapy circuit 320 to deliver a ventricular pacing pulse upon the expiration of the selected indicated pacing interval $S_n$.

Stated differently, for this embodiment, the ventricle is paced at the VRR indicated rate only if an atrial tachyarrhythmia, such as atrial fibrillation, is present and the VRR indicated rate exceeds the sensor indicated rate. Otherwise the ventricle is paced at the sensor indicated rate. If, for example, the patient is resting, such that the sensor indicated rate is lower than the patient's intrinsic rate, and no atrial tachyarrhythmia is present, then the device will sense the intrinsic rate or will deliver ventricular paces at the lower rate limit. But if, for example, the patient is resting, but with an atrial tachyarrhythmia that induces irregular ventricular contractions, then pacing pulses generally will be delivered at the VRR indicated rate. In another example, if the patient is active, such that the sensor indicated rate is higher than the VRR indicated rate, then pacing pulses generally will be delivered at the sensor indicated rate, whether or not atrial tachyarrhythmia is present As an alternative to the selection described with respect to Table 1, selection module 915 provides a fixed or variable weighting or blending of both the sensor-indicated rate and VRR indicated rate, such that pacing pulses are delivered based on the blended rate.

The second indicated pacing interval need not be based on sensor indications. In one embodiment, for example, the second indicated pacing interval tracks the sensed atrial heart rate when no atrial tachyarrhythmia is present. In this embodiment, selection module 915 performs a mode-switching function in which the first indicated pacing interval is used whenever atrial tachyarrhythmia is present and the second indicated pacing interval (e.g., atrial-tracking) is used when no atrial tachyarrhythmia is present.

In another embodiment, heart rate/interval is used as a trigger turn on/off use of the first indicated pacing interval (e.g., the VRR indicated pacing interval). In one example, pacing therapy is based on the first indicated pacing interval if the first indicated pacing interval is longer than a first predetermined value, and pacing therapy is substantially independent of the first indicated pacing interval if the first indicated pacing interval is shorter than the first predetermined value. In this example, the VRR indicated pacing interval is used at low heart rates, but not at fast heart rates.

Filter Rate Behavior Example 1

Figure 11:
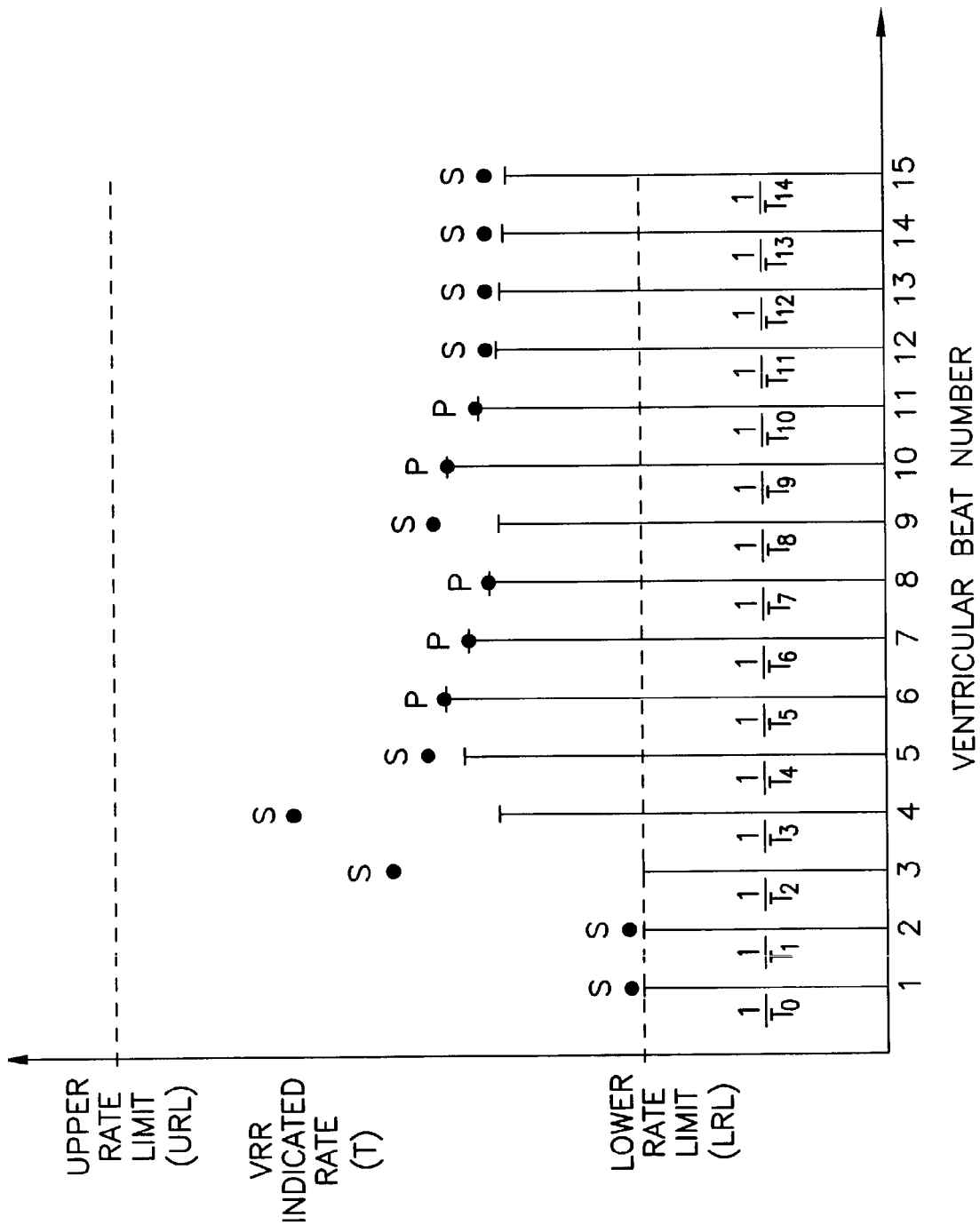
FIG. 11 is a graph illustrating generally one embodiment of operating a filter to provide a first indicated rate, such as a Ventricular Rate Regularization ("VRR") indicated rate, for successive ventricular heart beats.

FIG. 11 is a graph illustrating generally, by way of example, but not by way of limitation, one embodiment of a VRR indicated rate for successive ventricular heart beats for one mode of operating filter 515. As discussed above, the VRR indicated rate is simply the frequency, between ventricular heart beats, associated with the first indicated pacing interval. Stated differently, the VRR indicated rate is the inverse of the duration of the first indicated pacing interval. If pacing is based solely on the VRR indicated rate, pacing control module 505 directs ventricular therapy circuit 320 to issue a pacing pulse after the time since the last ventricular beat equals or exceeds the first indicated pacing interval. However, as described above, in certain embodiments, pacing control module 505 directs ventricular therapy circuit 320 to issue a pacing pulse based on factors other than the VRR indicated rate such as for, example, based on the sensor indicated rate.

In the example illustrated in FIG. 11, a first sensed intrinsic ventricular beat, indicated by an "S" was detected just before expiration of the first indicated pacing interval ("VRR indicated pacing interval") $T_0$, as computed based on a previous ventricular beat. In one embodiment, the new VRR indicated pacing interval $T_1$ is computed based on the duration of most recent V—V interval $VV_1$ and a previous value of the VRR indicated pacing interval $T_0$, as discussed above. In this example, the new VRR indicated pacing interval $T_1$ corresponds to a lower rate limit (LRL) time interval. In one embodiment, the allowable range of the VRR indicated pacing interval is limited so that the VRR indicated pacing interval does not exceed the duration of the LRL time interval, and so that the VRR indicated pacing interval is not shorter than the duration of an upper rate limit (URL) time interval.

The second ventricular beat is also sensed, just before expiration of the VRR indicated pacing interval $T_1$. In one embodiment, the new VRR indicated pacing interval $T_2$ is computed based on the duration of most recent V—V interval $VV_2$ and a previous value of the VRR indicated pacing interval, $T_1$, as discussed above. The first and second ventricular beats represent a stable intrinsic rhythm, for which no pacing is delivered because the VRR indicated pacing interval is at a lower rate than the sensed intrinsic ventricular beats.

The third, fourth, and fifth ventricular beats represent the onset of atrial fibrillation, resulting in erratic ventricular rates. The third ventricular beat is sensed well before expiration of the VRR indicated pacing interval $T_2$, such that no pacing pulse is issued. For the sensed third ventricular beat, filter 515 computes the new VRR indicated pacing interval $T_3$ as being shorter in duration relative to the previous VRR indicated pacing interval $T_2$.

The fourth ventricular beat is similarly sensed well before expiration of the VRR indicated pacing interval $T_3$, such that no pacing pulse is issued. For the sensed fourth ventricular beat, filter 515 computes the new VRR indicated pacing interval $T_4$ as being shorter in duration relative to the previous VRR indicated pacing interval $T_3$.

The fifth ventricular beat is sensed before expiration of the VRR indicated pacing interval $T_4$, such that no pacing pulse is issued. For the sensed fifth ventricular beat, filter 515 computes the new VRR indicated pacing interval $T_5$ as being shorter in duration relative to the previous VRR indicated pacing interval $T_4$.

The sixth, seventh, and eighth ventricular beats indicate regularization of the ventricular rate using the pacing techniques described above. No ventricular beat is sensed during the VRR indicated pacing interval $T_5$, so a pacing pulse is issued to evoke the sixth ventricular beat. A new VRR indicated pacing interval $T_6$ is computed as being increased in duration relative to the previous VRR indicated pacing interval $T_5$, lowering the VRR indicated rate. Similarly, no ventricular beat is sensed during the VRR indicated pacing interval.

The ninth ventricular beat represents another erratic ventricular beat resulting from the atrial fibrillation episode. The ninth ventricular beat is sensed before expiration of the VRR indicated pacing interval $T_8$. As a result, a shorter new VRR indicated pacing interval $T_9$ is computed.

The tenth and eleventh ventricular beats illustrate further regularization of the ventricular rate using the pacing techniques described above. No ventricular beat is sensed during the VRR indicated pacing interval $T_9$, so a pacing pulse is issued to evoke the tenth ventricular beat. A new VRR indicated pacing interval $T_{10}$ is computed as being increased in duration relative to the previous VRR indicated pacing interval $T_9$, lowering the VRR indicated rate. Similarly, no ventricular beat is sensed during the VRR indicated pacing interval $T_{10}$, so a pacing pulse is issued to evoke the tenth ventricular beat. A new VRR indicated pacing interval $T_{11}$ is compute as being increased in duration relative to the previous VRR indicated pacing interval $T_{10}$, lowering the VRR indicated rate.

The twelfth, thirteenth, fourteenth, and fifteenth ventricular beats illustrate resumption of a stable intrinsic rhythm after termination of the atrial fibrillation episode. For such a stable rate, the VRR indicated rate proceeds asymptotically toward a "floor value" that tracks, but remains below, the intrinsic rate. This allows the intrinsic heart signals to control heart rate when such intrinsic heart signals provide a stable rhythm. As a result, when the patient's intrinsic rate is constant, paces will be withheld, allowing the patient's intrinsic heart rhythm to continue. If the patient's heart rate includes some variability, and the VRR indicated floor value is close to the mean intrinsic heart rate, then occasional paced beats will occur. Such pace beats will gradually lengthen the VRR indicated pacing interval, thereby allowing subsequent intrinsic behavior when the patient's heart rate becomes substantially constant.

The intrinsic coefficient a of filter 515 controls the "attack slope" of the VRR indicated heart rate as the VRR indicated heart rate increases because of sensed intrinsic beats. The paced coefficient b of filter 515 controls the "decay slope" of the VRR indicated heart rate as the VRR indicated heart rate decreases during periods of paced beats. In one embodiment, in which a>1.0 and b>1.0, decreasing the value of a toward 1.0 increases the attack slope such that the VRR indicated rate increases faster in response to sensed intrinsic beats, while decreasing the value of b toward 1.0 decreases the decay slope such that the VRR indicated rate decreases more slowly during periods of paced beats. Conversely, for a>1.0 and b>1.0, increasing the value of a from 1.0 decreases the attack slope such that the VRR indicated rate increases more slowly in response to sensed intrinsic beats, while increasing the value of b from 1.0 increases the decay slope such that the VRR-indicated rate decreases more quickly during periods of paced beats.

In one embodiment, for a>1.0 and b>1.0, decreasing both a and b toward 1.0 increases VRR indicated rate during periods of sensed intrinsic activity so that the VRR indicated rate is closer to the mean intrinsic rate. Because the VRR indicated rate is closer to the mean intrinsic rate, variability in the intrinsic heart rate is more likely to trigger paces at the VRR indicated rate. On the other hand, for a>1.0 and b>1.0, increasing both a and b from 1.0 decreases the VRR indicated rate during periods of sensed intrinsic activity so that the VRR indicated rate is farther beneath the mean intrinsic rate. Because the VRR indicated rate is farther beneath the mean intrinsic rate, the same variability in the intrinsic heart rate becomes less likely to trigger paces at the VRR indicated rate.

In one embodiment, these coefficients are programmable by the user, such as by using remote programmer 125. In another embodiment, the user selects a desired performance parameter (e.g., desired degree of rate regularization, desired attack slope, desired decay slope, etc.) from a corresponding range of possible values, and device 105 automatically selects the appropriate combination of coefficients of filter 515 to provide a filter setting that corresponds to the selected user-programmed performance parameter, as illustrated generally by Table 2. Other levels of programmability or different combinations of coefficients may also be used.

TABLE 2

Example of Automatic Selection of Aspects of Filter Setting Based on a User-Programmable Performance Parameter.

| User-Programmable Performance Parameter | Intrinsic Coefficient a | Paced Coefficient b |
|---|---|---|
| 1 (Less Rate Regularization) | 2.0 | 3.0 |
| 2 | 1.8 | 2.6 |
| 3 | 1.6 | 2.2 |
| 4 | 1.4 | 1.8 |
| 5 | 1.2 | 1.4 |
| 6 (More Rate Regularization) | 1.0 | 1.0 |

Filter Rate Behavior Example 2

Figure 12:
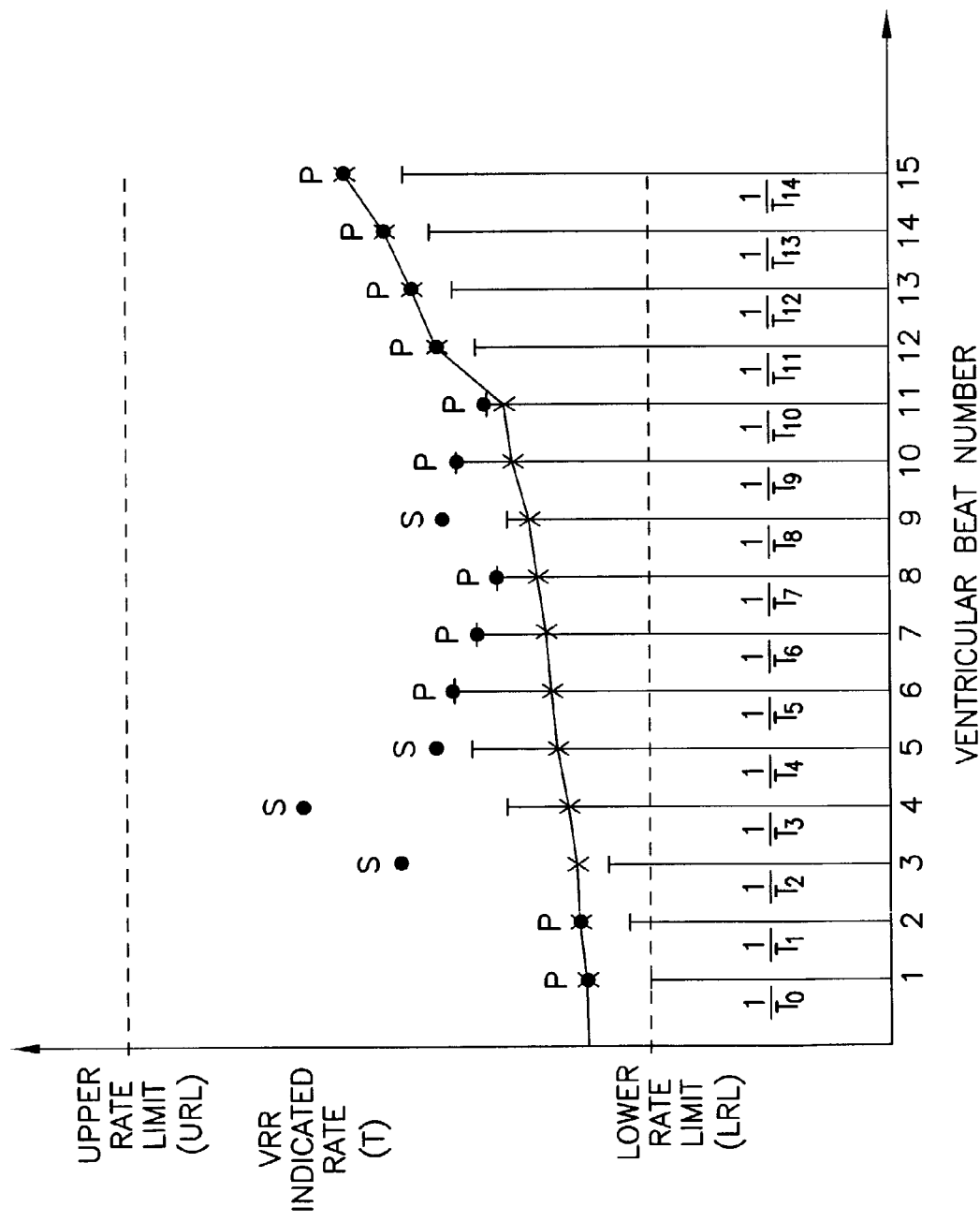
FIG. 12 is a graph illustrating generally another embodiment of operating a filter to provide a first indicated pacing rate, such as a VRR indicated rate, and delivering therapy based on the first indicated pacing rate and based on a second indicated pacing rate, such as a sensor indicated rate.

FIG. 12 is a graph illustrating generally, by way of example, but not by way of limitation, one embodiment of selecting between more than one indicated pacing interval. FIG. 12 is similar to FIG. 11 in some respects, but FIG. 12 includes a second indicated pacing interval. In one embodiment, the first indicated pacing interval is the VRR indicated pacing interval, described above, and the second indicated pacing interval is a sensor indicated pacing interval, from an accelerometer, minute ventilation, or other indication of the patient's physiological need for increased cardiac output.

In one embodiment, a selected indicated pacing interval is based on the shorter of the first and second indicated pacing intervals. Stated differently, device 105 provides pacing pulses at the higher indicated pacing rate. In the example illustrated in FIG. 12, first and second beats and the twelfth through fifteenth beats are paced at the sensor indicated rate, because it is higher than the VRR indicated rate and the intrinsic rate. The third, fourth, fifth, and ninth beats are sensed intrinsic beats that are sensed during the shorter of either of the VRR and sensor indicated pacing intervals. The sixth through eighth beats and ninth and tenth beats are paced at the VRR indicated rate, because it is higher than the sensor indicated rate. Also, for these beats, no intrinsic beats are sensed during the VRR indicated intervals. In this embodiment, the ranges of both the sensor indicated rate and the VRR indicated rate are limited so that they do not extend to rates higher than the URL or to rates lower than the LRL. In one embodiment, the LRL and the URL are programmable by the user, such as by using remote programmer 125.

In a further embodiment, the selected indicated pacing interval is based on the shorter of the first and second indicated pacing intervals only if an atrial tachyarrhythmia, such as atrial fibrillation, is present. Otherwise, the second indicated pacing interval is used, as described above.

Filter Rate Behavior Example 3

Figure 13:
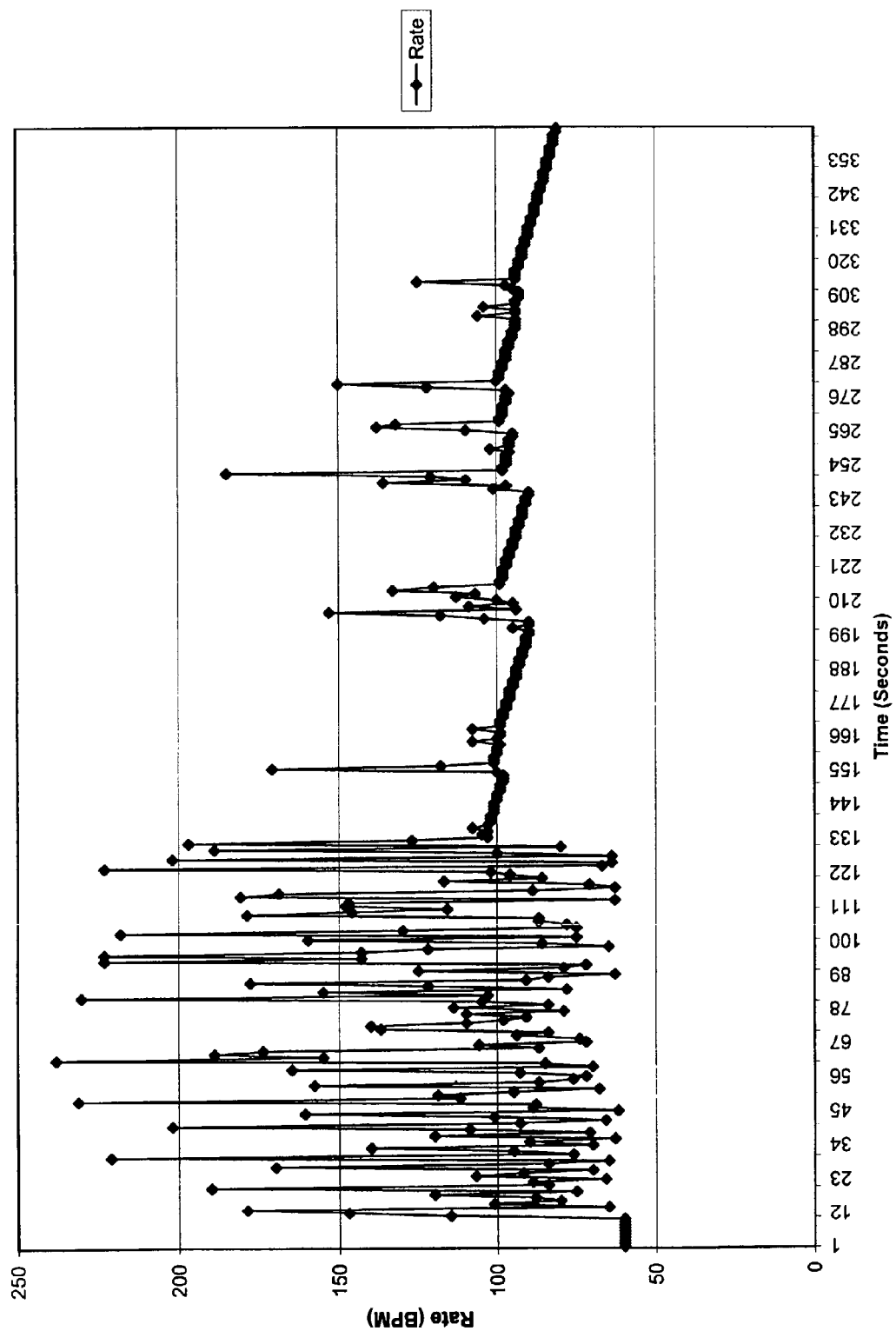
FIG. 13 is a graph illustrating generally another illustrative example of heart rate vs. time according to a VRR algorithm spreadsheet simulation.

FIG. 13 is a graph illustrating generally, by way of example, but not by way of limitation, another illustrative example of heart rate vs. time according to a spreadsheet simulation of the behavior of the above-described VRR algorithm. In FIG. 13, the VRR algorithm is turned off until time 130. Stable intrinsic lower rate behavior is modeled for times between 0 and 10 seconds. Erratic intrinsic ventricular rates, such as would result from atrial tachyarrhythmias including atrial fibrillation, are modeled during times between 10 seconds and 130 seconds. At time 130 seconds, the VRR algorithm is turned on. While some erratic intrinsic beats are subsequently observed, the VRR algorithm provides pacing that is expected to substantially stabilize the heart rate, as illustrated in FIG. 13. The VRR indicated pacing rate gradually decreases until intrinsic beats are sensed, which results in a slight increase in the VRR indicated pacing rate. Thus, the VRR algorithm favors the patient's intrinsic heart rate when it is stable, and paces at the VRR indicated heart rate when the patient's intrinsic heart rate is unstable. It is noted that FIG. 13 does not represent clinical data, but rather provides a simulation model that illustrates one example of how the VRR algorithm is expected to operate.

Filter Example 4

In one embodiment, filter 515 includes variable coefficients such as, for example, coefficients that are a function of heart rate (or its corresponding time interval). In one example, operation of the filter 515 is described by $T_n = a \cdot w \cdot VV_n + (1-w) \cdot T_{n-1}$, if $VV_n$ is concluded by an intrinsic beat, otherwise is described by $T_n = b \cdot w \cdot VV_n + (1-w) \cdot T_{n-1}$, if $VV_n$ is concluded by a paced beat, where at least one of a and b are linear, piecewise linear, or nonlinear functions of one or more previous V—V intervals such as, for example, the most recent V—V interval, $VV_n$.

Figure 14:
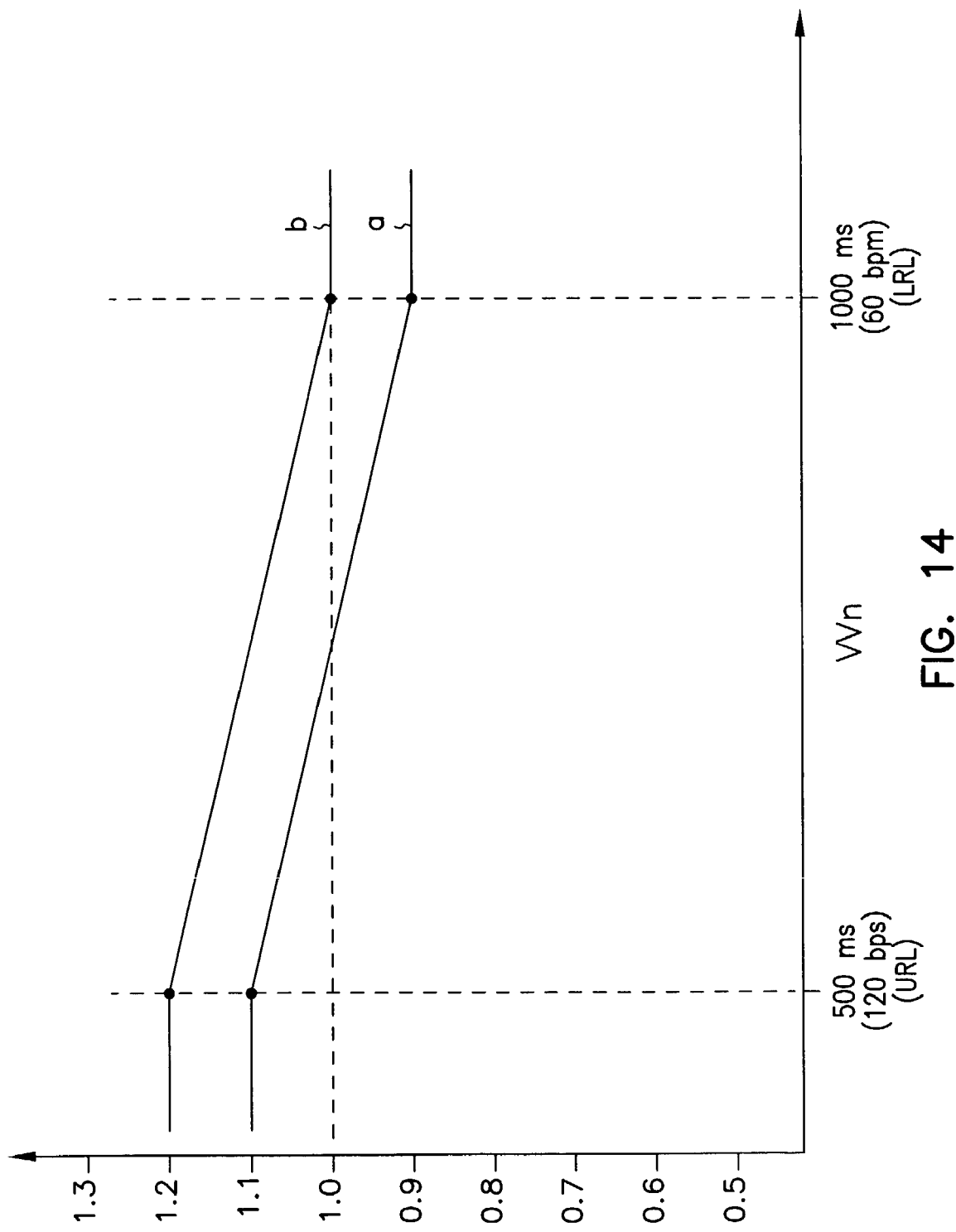
FIG. 14 is a graph illustrating generally one embodiment of using at least one of coefficients a and b as a function of heart rate (or corresponding time interval).

FIG. 14 is a graph illustrating generally, by way of example, but not by way of limitation, one embodiment of using at least one of coefficients a and b as a function of one or more previous V—V intervals such as, for example, the most recent V—V interval, $VV_n$. In one such example, a is less than 1.0 when $VV_n$ is at or near the lower rate limit (e.g., 1000 millisecond interval or 60 beats/minute), and a is greater than 1.0 when $VV_n$ is at or near the upper rate limit (e.g., 500 millisecond interval or 120 beats/minute). For a constant b, using a smaller value of a at lower rates will increase the pacing rate more quickly for sensed events; using a larger value of a at higher rates increases the pacing rate more slowly for sensed events. In another example, b is close to 1.0 when $VV_n$ is at or near the lower rate limit, and b is greater than 1.0 when $VV_n$ is at or near the upper rate limit. For a constant a, using a smaller value of b at lower rates will decrease the pacing rate more slowly for paced events; using a larger value of b at higher rates decreases the pacing rate more quickly for paced events.

USING VRR FOR OPTIMIZING TIMING OF ATRIAL CARDIOVERSION/DEFIBRILLATION THERAPY

Figure 15:
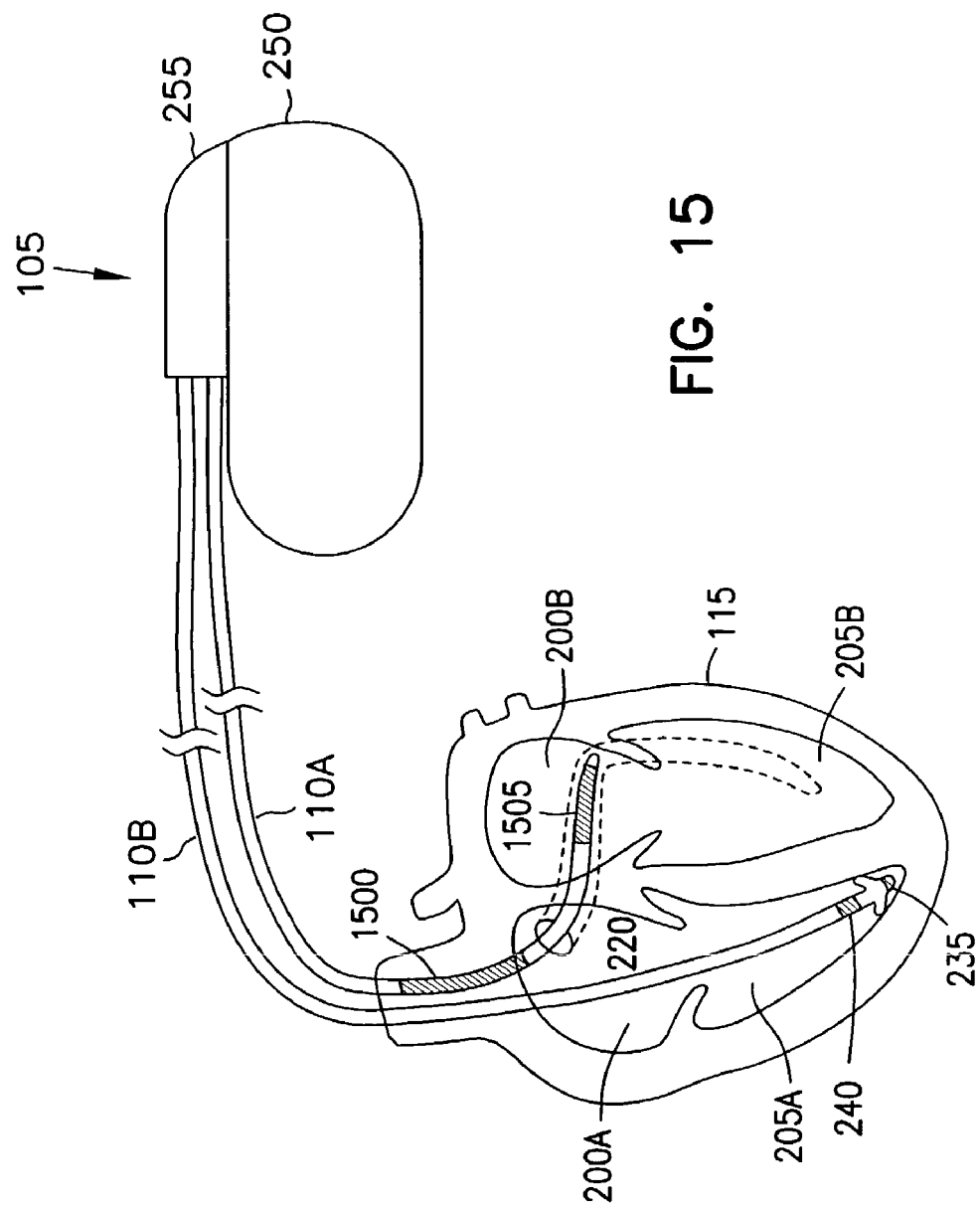
FIG. 15 is a schematic diagram illustrating generally another embodiment of a cardiac rhythm management device which is coupled to a heart.

FIG. 15 is a schematic diagram, similar to FIG. 2, illustrating generally, by way of example, but not by way of limitation, another embodiment of portions of system 100 and an environment in which it is used. In this embodiment, atrial lead 110A includes electrodes disposed in, around, or near right atrium 200A of heart 115, such as superior vena cava (SVC) ring electrode 1500 and coronary sinus (CS) ring electrode 1505 for delivering cardioversion/defibrillation therapy to right atrium 200A. Atrial lead 110A may also include additional electrodes, such as for sensing intrinsic heart signals and for delivering atrial or ventricular pacing or cardioversion/defibrillation therapy to heart 115. Alternatively, electrodes for sensing intrinsic atrial heart signals and delivering atrial pacing therapy are included on a separate lead disposed in right atrium 200A, as illustrated in FIG. 2. Moreover, additional electrodes may be located elsewhere, for sensing or delivering pacing or cardioversion/defibrillation therapy, such as using a portion of the can of hermetically sealed device 105 or using an electrode at a header portion extending therefrom.

Figure 16:
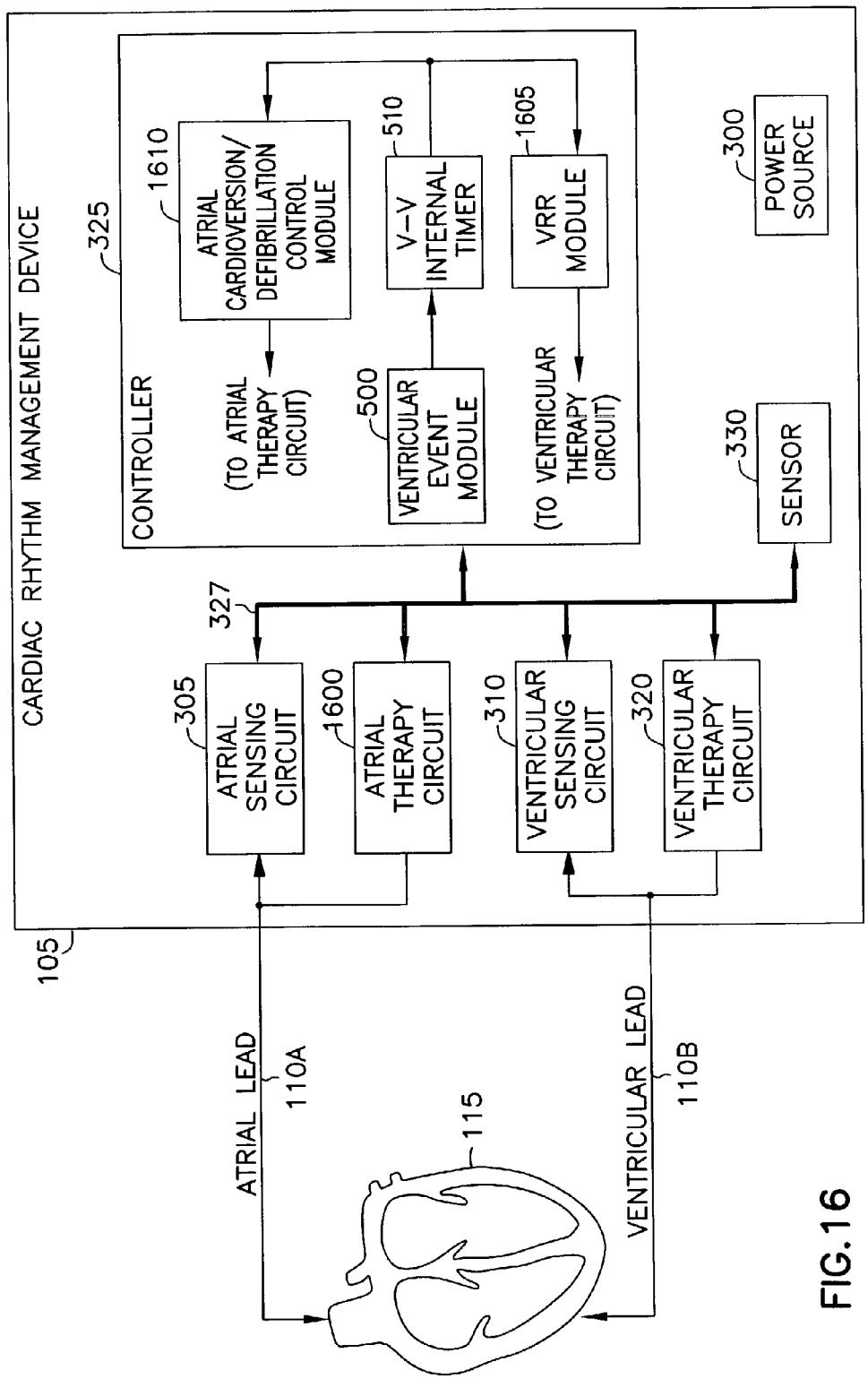
FIG. 16 is a schematic diagram illustrating generally another embodiment of portions of a cardiac rhythm management device which is coupled to a heart.

FIG. 16 is a schematic diagram, similar to FIG. 3, illustrating generally, by way of example, but not by way of limitation, another embodiment of portions of device 105, which is coupled to heart 115. In this embodiment, device 105 includes an atrial therapy circuit 1600 providing atrial cardioversion/defibrillation therapy, as appropriate, to electrodes located at or near one of the atria 200 of heart 115, for terminating atrial fibrillation or other atrial tachyarrhythmias. In order, embodiment, atrial therapy circuit 1600 also provides atrial pacing therapy to electrodes located at or near one of the atria 200 of heart 115 for obtaining resulting evoked atrial depolarizations, i.e., paced atrial beats.

Controller 325 controls the delivery of therapy, by atrial therapy circuit 1600 and ventricular therapy circuit 320, based on heart activity signals received from atrial sensing circuit 305 and ventricular sensing circuit 310, as discussed below. Controller 325 includes various modules, which are implemented either in hardware or as one or more sequences of steps carried out on a microprocessor or other microcontroller. Though such modules are illustrated separately for conceptual clarity, it is understood that the various modules of controller 325 need not be separately embodied, but may be combined or otherwise implemented differently, such as in software/firmware.

In one embodiment, controller 325 includes a V—V interval timer 510, for measuring time intervals ("V—V intervals") between successive ventricular depolarizations obtained from ventricular event module 500. The V—V intervals are provided to VRR module 1605, which performs the ventricular rate regularization techniques described above with respect to FIGS. 5–14. In one embodiment, detection of an atrial tachyarrhythmia by atrial sensing circuit 305 triggers the regularization of the ventricular rate using VRR techniques. In another embodiment, however, VRR techniques are used even when no atrial tachyarrhythmia is present. V—V interval timer 510 also provides the V—V intervals to atrial cardioversion/defibrillation control module 1610, which evaluates the V—V intervals based on certain criteria to determine whether potentially proarrhythmic heart conditions exist. If such potentially proarrhythmic heart conditions exist, atrial cardioversion/defibrillation module 1610 withholds atrial cardioversion/defibrillation therapy until VRR module 1605 suitably stabilizes the ventricular heart rate using the VRR techniques.

Example Method of Operating Cardiac Rhythm Management Device

The present system recognizes that atrial tachyarrhythmias typically cause significant variability in the ventricular heart rate. Device 105 avoids delivering atrial cardioversion/defibrillation therapy during such irregular ventricular heart activity, because such conditions may be potentially proarrhythmic, such that delivering atrial cardioversion/defibrillation therapy could result in dangerous ventricular arrhythmias. Using the VRR techniques described above, device 105 stabilizes the ventricular heart rate to obtain less potentially proarrhythmic conditions for delivering the atrial tachyarrhythmia therapy as a result of the more regular ventricular heart rate. Device 105 withholds delivery of atrial cardioversion/defibrillation therapy until the V—V intervals meet certain criteria that indicate a decreased chance that the atrial cardioversion/defibrillation therapy will induce a ventricular arrhythmia.

Figure 17:
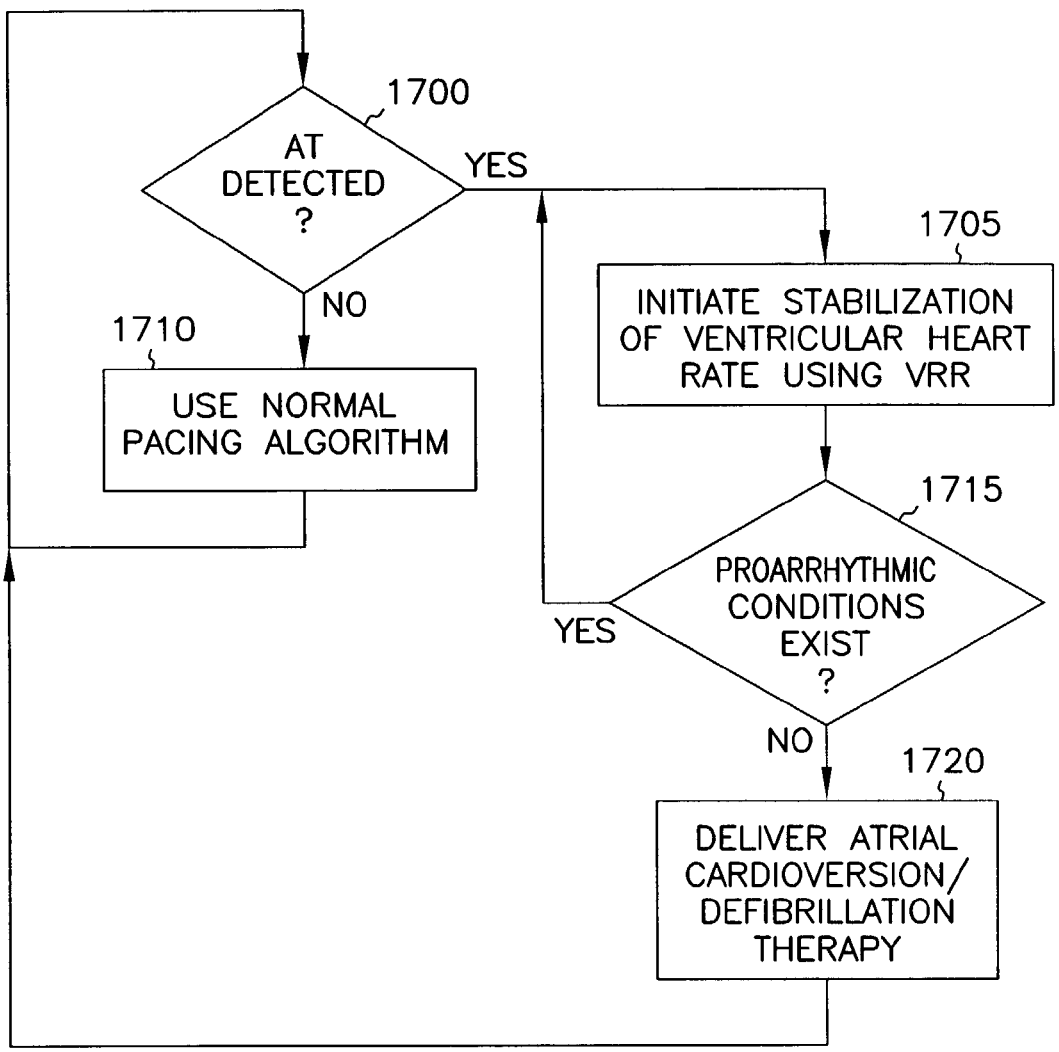
FIG. 17 is a flow chart illustrating generally one embodiment of operating a cardiac rhythm management device for delivering atrial cardioversion/defibrillation therapy to terminate an atrial tachyarrhythmia, such as atrial fibrillation, and enable the resumption of normal atrial heart rhythms.

FIG. 17 is a flow chart illustrating generally, by way of example, but not by way of limitation, one embodiment of operating device 105 for delivering atrial cardioversion/defibrillation therapy to terminate an atrial tachyarrhythmia, such as atrial fibrillation, and enable the resumption of normal atrial heart rhythms.

At step 1700, atrial sensing circuit 305 is used to detect an atrial tachyarrhythmia, such as atrial fibrillation. If atrial fibrillation is detected at step 1700, then step 1705 initiates stabilization of the ventricular heart rate, using the VRR techniques discussed above, in order to obtain conditions that are not potentially proarrhythmic. (As described above, in one embodiment, VRR stabilization techniques provide pacing that overdrives the intrinsic ventricular heart rate unless the intrinsic ventricular heart rate is substantially regular). If atrial fibrillation is not detected at step 1700, then at step 1710, a conventional pacing algorithm is used to determine whether pacing therapy should be delivered to the heart 115.

Step 1715 performs a beat-by-beat determination of whether potentially proarrhythmic conditions exist in the ventricle, based on the V—V time interval between paced or sensed ventricular events. One embodiment of performing step 1715 is described more particularly below with respect to FIG. 18. If step 1715 indicates that no potentially proarrhythmic conditions exist, then atrial cardioversion/defibrillation therapy is delivered in step 1720. Otherwise, potentially proarrhythmic conditions do exist, and such atrial-cardioversion/defibrillation therapy is withheld (i.e., step 1720 is bypassed) until no potentially proarrhythmic conditions exist, with stabilization of the ventricular heart rate using VRR continuing at step 1705. Stabilization of the ventricular heart rate, at step 1705, more quickly obtains conditions that are not potentially proarrhythmic, because the VRR techniques promote ventricular pacing at a rate that is close to the mean intrinsic ventricular heart rate during periods of erratic intrinsic ventricular heart rates. This, in turn, stabilizes the ventricular heart rate, as described above, more quickly obtaining conditions that are not potentially proarrhythmic.

In one embodiment, delivery of the atrial cardioversion/defibrillation therapy at step 1720 is synchronized to the most recent ventricular beat, i.e., the ventricular beat that concludes $VV_n$. In one example, if the most recent ventricular beat is a paced beat, then, at step 1720, a defibrillation countershock is delivered to the right atrium 200A within approximately 20 to 150 milliseconds (e.g., 70 milliseconds) after the pacing pulse was delivered. In this same example, if the most recent ventricular beat is a sensed beat, then, at step 1720, a defibrillation countershock is delivered to the right atrium 200A during the QRS complex of the sensed ventricular beat. In one embodiment, an atrial defibrillation countershock of approximately between 1 Joule and 25 Joules (e.g., approximately 4 Joules) is delivered between electrode 1505 located in or near coronary sinus 220 and an electrode 1500 located in a supra ventricular region such as in or near the superior vena cava. In another embodiment, the atrial defibrillation countershock is delivered between an electrode 1505 located in or near coronary sinus 220 and a pair of intercoupled electrodes located (1) in or near coronary sinus 220 and (2) at device 105 or header 225.

By stabilizing the ventricular heart rate before delivering atrial cardioversion/defibrillation therapy, device 105 promotes conditions that not potentially proarrhythmic, such that atrial cardioversion/defibrillation therapy can be safely delivered at step 1720. Thus, device 105 advantageously actively stabilizes the heart to obtain conditions that are not potentially proarrhythmic, and does so more quickly than if the heart were not actively stabilized. The stabilization is performed using the VRR techniques described above. In one embodiment, the VRR techniques stabilize the ventricular rate at a variable rate that is based at least in part on the patient's underlying intrinsic rate; the VRR indicated rate is based on either intrinsic or evoked ventricular activations, or both.

Because the ventricular rate stabilization is based on the patient's underlying intrinsic ventricular rate, as determined using the VRR techniques described above, device 105 ensures that the ventricular pacing rate will be high enough to stabilize the ventricular heart rate during periods of erratic intrinsic ventricular activity. Moreover, because the ventricular pacing rate is based on the intrinsic ventricular rate, the patient need not be paced at excessive ventricular rates when stabilizing intrinsic ventricular heart activity.

Figure 18:
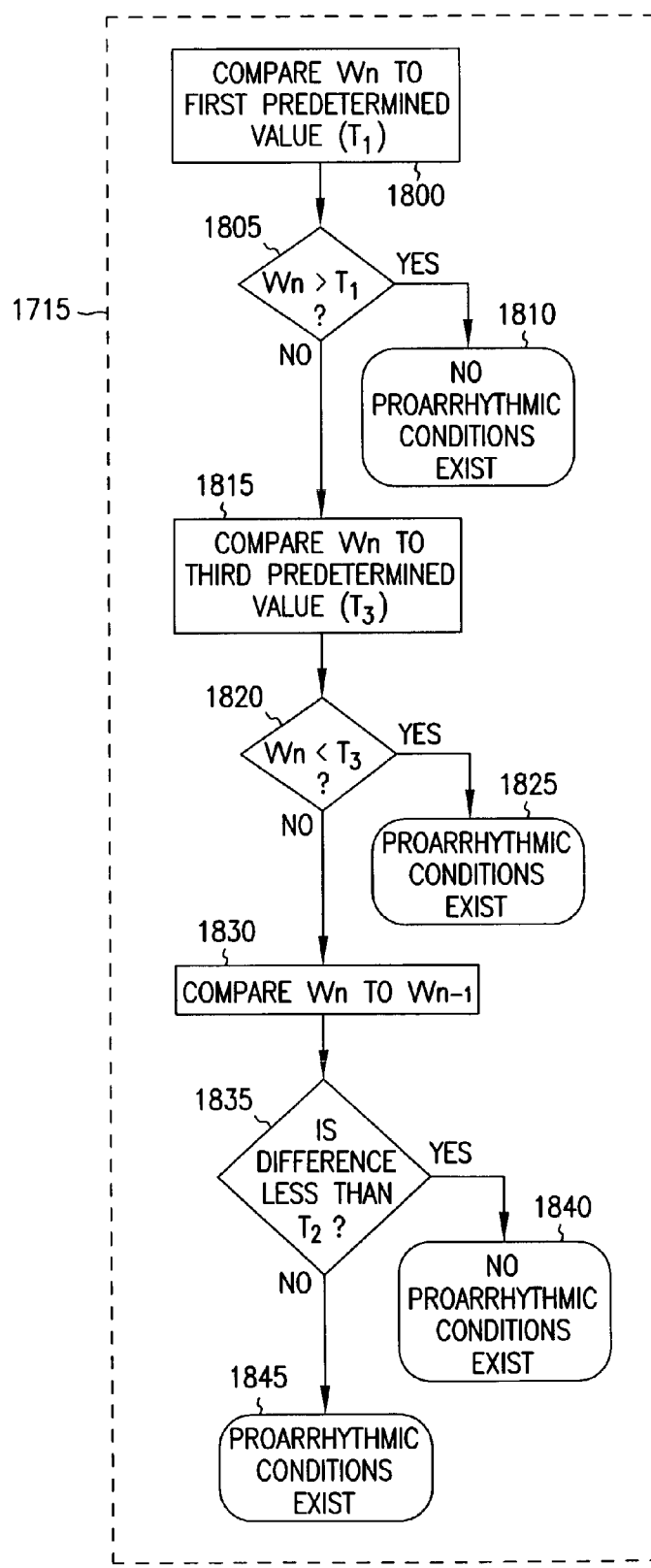
FIG. 18 is a flow chart illustrating generally one embodiment of determining whether potentially proarrhythmic conditions exist.

FIG. 18 is a flow chart that illustrates generally, by way of example, but not by way of limitation, one embodiment of determining whether potentially proarrhythmic conditions exist at step 1715 of FIG. 17. FIG. 18 illustrates one embodiment of a sequence of substeps underlying decision block 1715 in FIG. 17. In FIG. 18, at step 1800, the most recent V—V interval, $VV_n$, is compared to a first predetermined value, $T_1$. At step 1805, if $VV_n$ is greater than $T_1$ (or, in an alternate embodiment, greater than or equal to $T_1$), then at step 1810 the algorithm deems that no potentially proarrhythmic conditions exist. Otherwise, at step 1815, $VV_n$ is compared to a third predetermined value, $T_3$. At step 1820, if $VV_n$ is less than $T_3$ (or, in an alternate embodiment, less than or equal to $T_3$), then at step 1825 the algorithm deems that potentially proarrhythmic conditions do exist. Otherwise, at step 1830 the most recent V—V interval, $VV_n$, is compared to the previous V—V interval, $VV_{n-1}$. At step 1835, if the difference between $VV_n$ and $VV_{n-1}$ less than a second predetermined value, $T_2$ (or, in an alternate embodiment, less than or equal to $T_2$), then at step 1840 the algorithm deems that no potentially proarrhythmic conditions exist. Otherwise, at step 1845, the algorithm deems that potentially proarrhythmic conditions do exist.

Figure 19:
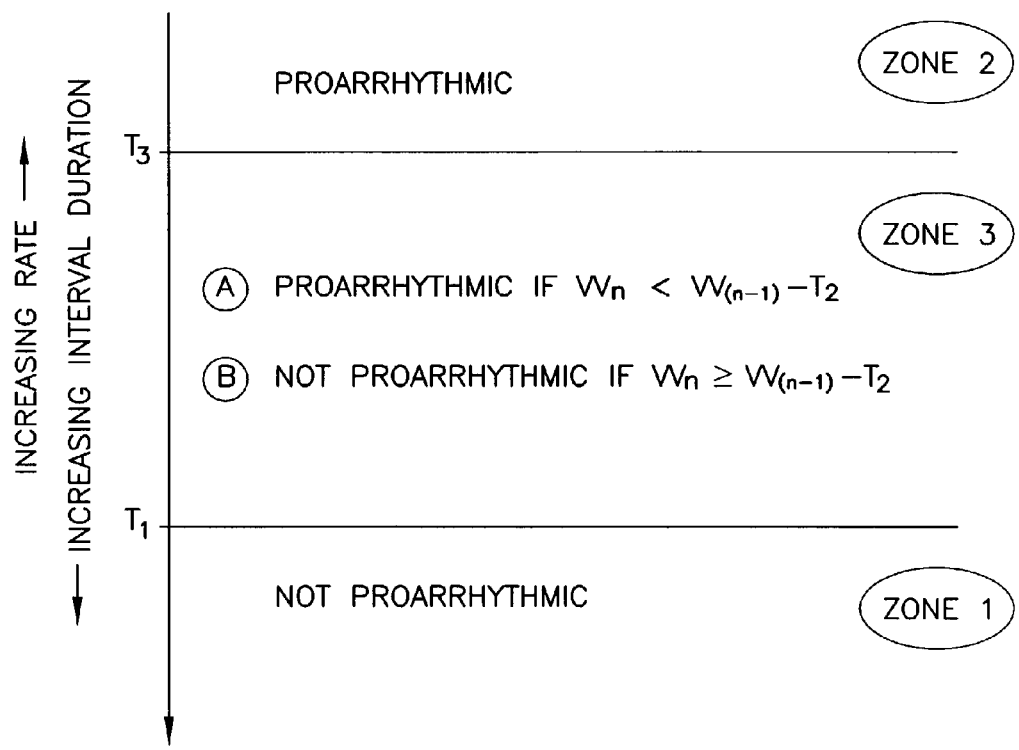
FIG. 19 is a chart further illustrating generally one embodiment of determining whether potentially proarrhythmic conditions exist, such as described with respect to FIG. 18.

FIG. 19 is a chart that illustrates generally, by way of example, but not by way of limitation, one embodiment of determining whether potentially proarrhythmic conditions exist, such as described with respect to FIG. 18. In FIG. 19, the Y-axis indicates increasing ventricular heart rate in a first direction, and increasing V—V interval duration in a second direction opposite to the first, as a result of the inverse relationship between rate and interval. In Zone 1, if the most recent V—V interval, $VV_n$, is longer than (or alternatively, longer than or equal to) $T_1$ (e.g., $T_1=800$ milliseconds), then the algorithm deems that no potentially proarrhythmic conditions exist in the ventricle. In Zone 2, if the most recent V—V interval, $VV_n$, is shorter than (or alternatively, shorter than or equal to) $T_3$ (e.g., $T_3=500$ milliseconds), then the algorithm deems that potentially proarrhythmic conditions do exist in the ventricle. In Zone 3, for $VV_n$ between $T_n$ and $T_3$ (or alternatively, within such range including the endpoints $T_1$ and $T_3$), then a further comparison is made between the most recent V—V interval, $VV_n$, and the previous V—V interval, $VV_{n-1}$. If the magnitude of the difference between $VV_n$ and $VV_{n-1}$ is less than $T_2$ (or alternatively, less than or equal to $T_2$), then the algorithm deems that potentially proarrhythmic conditions do not exist (condition "B"); otherwise, the algorithm deems that potentially proarrhythmic conditions do exist (condition "A"). When the ventricular heart rate is in Zone 3, use of the VRR techniques in step 1705 of FIG. 17 promotes condition B over condition A, because VRR stabilizes the ventricular heart rate, thereby reducing the time differences between successive V—V intervals. Thus, stabilization of the ventricular heart rate using the VRR techniques promotes conditions that are not potentially proarrhythmic, so that atrial cardioversion/defibrillation therapy can be delivered quickly, but also safely, i.e., without risking inducing a ventricular tachyarrhythmia. Moreover, stabilization of the ventricular heart rate using VRR techniques quickly obtains a regular ventricular heart rhythm because, as explained above, the VRR stabilization is based on the underlying intrinsic heart rate and, in one embodiment, uses an IIR filter than establishes a VRR-indicated rate based on the most recent V—V interval, $VV_n$, and a previous value of the VRR-indicated rate.

In one embodiment, $T_1$ is programmable to values approximately between 700 milliseconds and 1000 milliseconds, with a default value of approximately 800 milliseconds. In this embodiment, $T_3$ is programmable to values that are less than (or, alternatively, less than or equal to) $T_1$ and in the range approximately between 350 milliseconds and 1000 milliseconds, with $T_3$ having a default value of approximately 500 milliseconds. Also in this embodiment, $T_2$ is programmable to values that are approximately between 0 milliseconds and 200 milliseconds, with $T_2$ having a default value of approximately 90 milliseconds. The values of these time intervals are illustrative only, and not intended to be restrictive.

Figure 20:
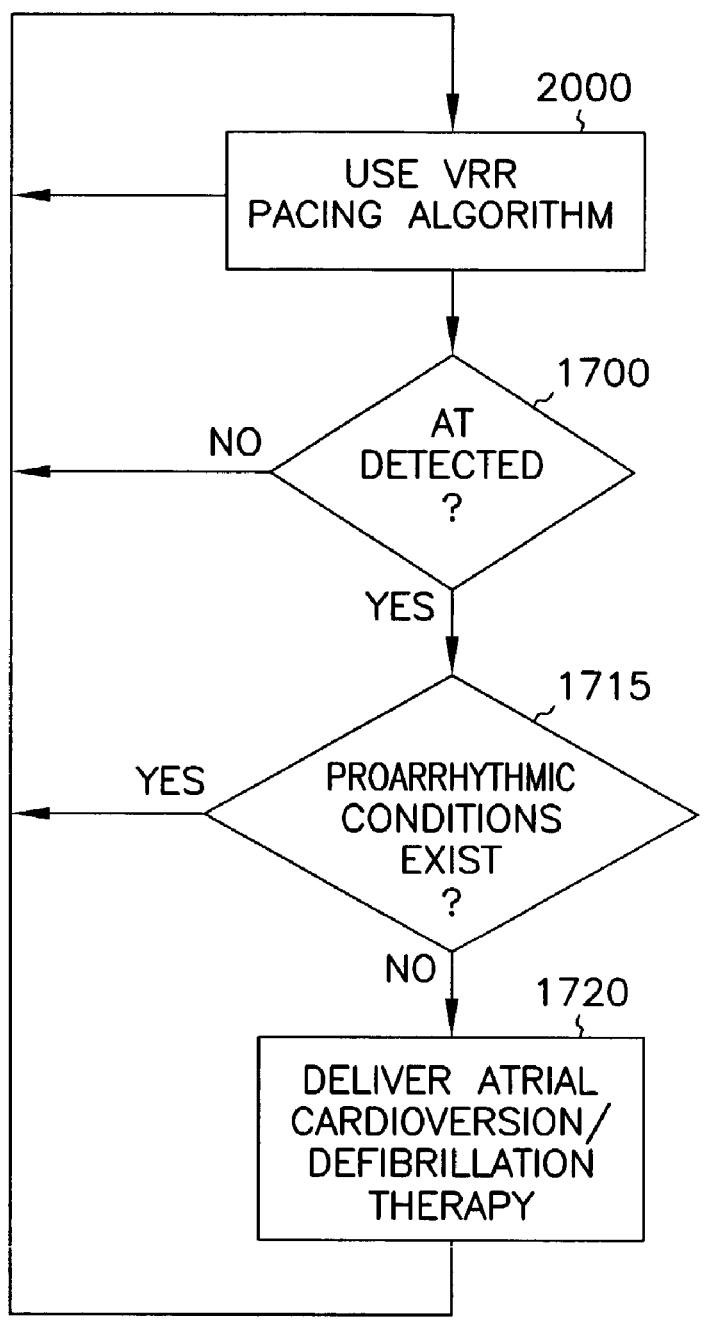
FIG. 20 is a flow chart, similar to FIG. 17, illustrating generally an embodiment of operating a cardiac rhythm management device in which stabilization of the ventricular heart rate using the VRR algorithm is independent of whether atrial tachyarrhythmias are detected.

FIG. 20 is a flow chart, similar to FIG. 17, illustrating generally, by way of example, but not by way of limitation, an embodiment of operating device 105 in which stabilization of the ventricular heart rate using the VRR algorithm is independent of whether atrial tachyarrhythmias are detected. At step 2000, pacing therapy is delivered to the ventricle at the VRR-indicated rate (either alone, or in combination with a sensor-indicated rate, as described above) even if no atrial tachyarrhythmia is present. At step 1700, if an atrial tachyarrhythmia (AT) such as atrial fibrillation is detected, and no potentially proarrhythmic conditions exist at step 1715, then device 105 provides atrial cardioversion/defibrillation therapy at step 1720. If no atrial tachyarrhythmia is detected at step 1700 or if potentially proarrhythmic conditions exist at step 1715, then device 105 withholds atrial cardioversion/defibrillation therapy (i.e., step 1720 is bypassed) and continues to provide pacing at the VRR-indicated rate at step 2000. As a result, atrial cardioversion/defibrillation therapy is only delivered at step 1720 if the atrial tachyarrhythmia exists in the absence of potentially proarrhythmic conditions. By using the VRR pacing algorithm in step 2000, the ventricular heart rate is stabilized to obtain conditions that are not potentially proarrhythmic so that atrial cardioversion/defibrillation therapy is delivered quickly and safely. In summary, while FIG. 17 illustrates using VRR only when an atrial tachyarrhythmia is detected (also referred to as "fallback to VRR" initiated by AT), FIG. 20 illustrates using VRR to determine the indicated ventricular heart rate even when atrial tachyarrhythmias are not present.

Figure 21:
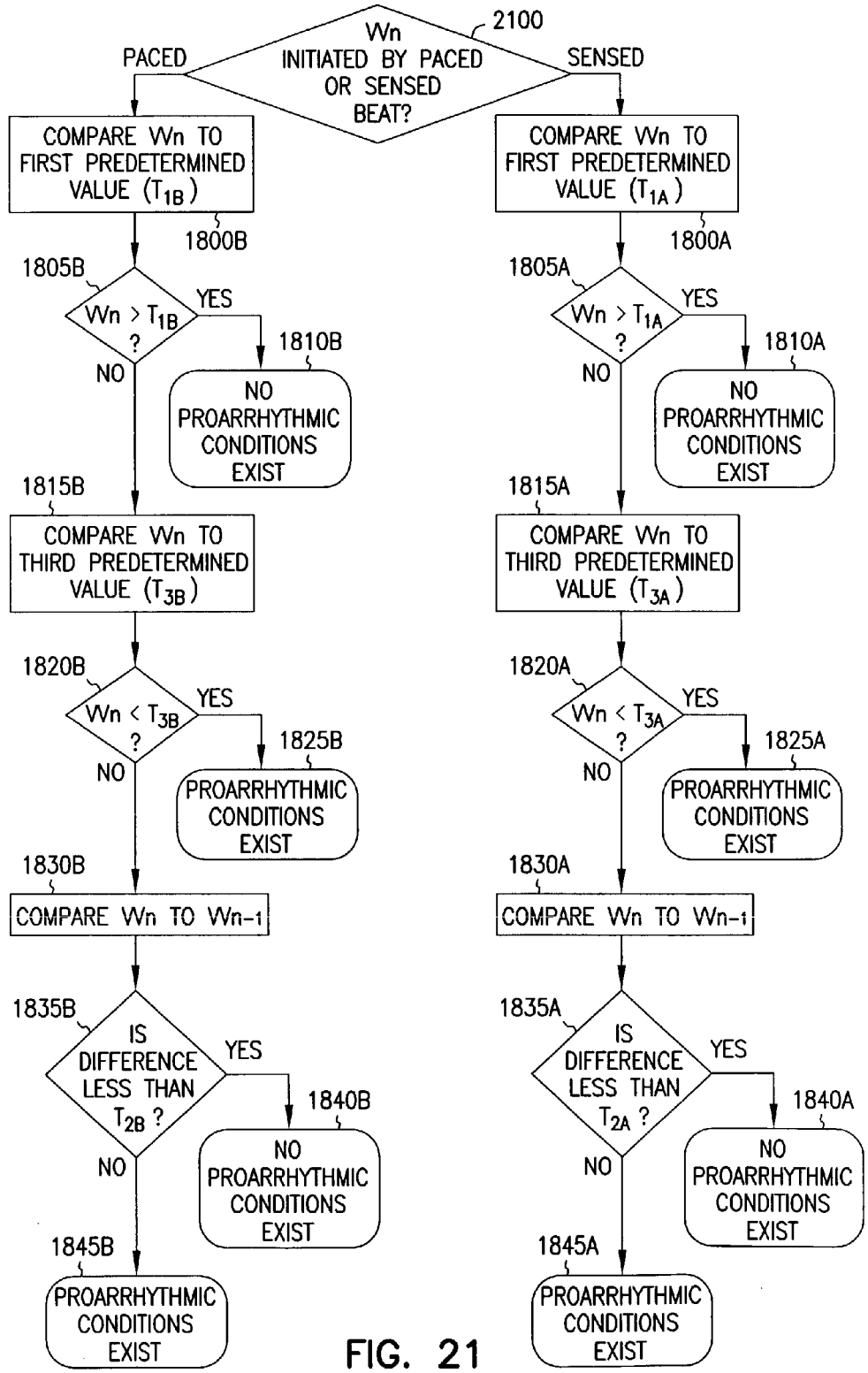
FIG. 21 is a flow chart, similar to FIG. 18, illustrating generally an embodiment of operating a cardiac rhythm management device using different comparison values for sensed and paced ventricular beats.

FIG. 21 is a flow chart, similar to FIG. 18, illustrating generally, by way of example, but not by way of limitation, an embodiment of operating device 105 in which one or more of the predetermined values to which V—V intervals are compared is different if $VV_n$ is initiated by a paced ventricular beat than if $VV_n$ is initiated by a sensed ventricular beat, as determined in step 2100. In one embodiment, the algorithm uses a longer first predetermined value $T_{1B}$ when $VV_n$ is initiated by a paced beat than the corresponding first predetermined value $T_{1A}$ when $VV_n$ is initi- ated by a sensed beat. This is because a paced beat is followed by a refractory period during which time the ventricular sensing circuit is disconnected from ventricular lead 110B to avoid saturating the ventricular sense amplifier circuits as a result of the after-potentials produced by delivering a pacing pulse. Because device 105 is "blind" to ventricular depolarizations occurring during the post-pace refractory period, the most recent V—V interval, if $VV_n$ is initiated by a paced ventricular beat, it is compared to a first predetermined value $T_{1B}$ that is longer than the first predetermined value $T_{1A}$ corresponding to a most recent V—V interval, $VV_n$ initiated by a sensed ventricular beat. Similarly, in one embodiment, the third predetermined value $T_{3B}$ is longer when $VV_n$ is initiated by a paced beat than the third predetermined value $T_{3A}$ when $VV_n$ is initiated by a sensed beat. This accounts for the additional time during which device 105 is "blind" following a paced ventricular beat. Similarly, in another embodiment, the second predetermined value $T_{3B}$ is longer when $VV_n$ is initiated by a paced beat than the second predetermined value $T_{3B}$ when $VV_n$ is initiated by a sensed beat.

CONCLUSION

The above-described system provides, among other things, atrial shock timing optimization. The system detects an atrial tachyarrhythmia, such as atrial fibrillation. Such atrial tachyarrhythmias typically cause significant variability in the ventricular heart rate. The system avoids delivering atrial cardioversion/defibrillation therapy during such irregular ventricular heart activity, because such conditions may be potentially proarrhythmic, such that delivering atrial cardioversion/defibrillation therapy could result in dangerous ventricular arrhythmias. Using Ventricular Rate Regularization ("VRR") techniques described above, the system stabilizes the ventricular heart rate to obtain less potentially proarrhythmic conditions for delivering the atrial tachyarrhythmia therapy. The system withholds delivery of atrial cardioversion/defibrillation therapy until the intervals between ventricular beats ("V—V intervals") meet certain criteria that decrease the chance that the atrial cardioversion/defibrillation therapy will induce a ventricular arrhythmia.

It is to be understood that the above description is intended to be illustrative, and not restrictive. Many other embodiments will be apparent to those of skill in the art upon reviewing the above description. The scope of the invention should, therefore, be determined with reference to the appended claims, along with the full scope of equivalents to which such claims are entitled.

What is claimed is:

1. A method comprising:
  computing a present indicated ventricular pacing interval, using infinite-impulse response (IIR) filtering, the filtering using as inputs: (1) a most recent V—V interval duration between ventricular events; and (2) a previously-computed value of the indicated ventricular pacing interval that corresponds to a V—V interval that immediately precedes the most recent V—V interval, the IIR filtering providing, as an output, the present indicated ventricular pacing interval;
  pacing a ventricle using the present indicated ventricular pacing interval;
  detecting an atrial tachyarrhythmia;
  determining whether potentially proarrhythmic conditions exist in the ventricle; and
  after the pacing the ventricle, the detecting the atrial tachyarrhythmia, and the determining whether potentially proarrhythmic conditions exist, then delivering cardioversion/defibrillation therapy to the atrium if it is determined that no potentially proarrhythmic conditions exist in the ventricle, otherwise withholding the delivery of cardioversion/defibrillation therapy to the atrium until it is determined that no potentially proarrhythmic conditions exist in the ventricle.

2. The method of claim 1, in which the determining whether potentially proarrhythmic conditions exist in the ventricle comprises:
   comparing the most recent V—V interval to a first predetermined value;
      deeming no potentially proarrhythmic conditions to exist if the most recent V—V interval is longer than a first predetermined value;
      deeming no potentially proarrhythmic conditions to exist if the most recent V—V interval is shorter than the first predetermined value and the most recent V—V interval exceeds or equals a preceding V—V interval less a second predetermined value;
   deeming potentially proarrhythmic conditions to exist if the most recent V—V interval is shorter than a third predetermined value; and
      deeming potentially proarrhythmic conditions to exist if the most recent V—V interval is longer than the third predetermined value and the most recent V—V interval is shorter than the preceding V—V interval less the second predetermined value.

3. The method of claim 2, in which the determining whether potentially proarrhythmic conditions exist in the ventricle further comprises:
   deeming potentially proarrhythmic conditions to exist if the most recent V—V interval is equal to the third predetermined value; and
   deeming no potentially proarrhythmic conditions to exist if the most recent V—V interval is equal to the first predetermined value.

4. The method of claim 2, in which the first predetermined value is approximately between 700 milliseconds and 1000 milliseconds.

5. The method of claim 2, in which the first predetermined value is different when the most recent V—V interval is initiated by a sensed beat than when the most recent V—V interval is initiated by a paced beat.

6. The method of claim 2, in which the second predetermined value is approximately between 0 milliseconds and 200 milliseconds.

7. The method of claim 2, in which second predetermined value is different when the most recent V—V interval is initiated by a sensed beat than when the most recent V—V interval is initiated by a paced beat.

8. The method of claim 2, in which the third predetermined value is different when the most recent V—V interval is initiated by a sensed beat than when the most recent V—V interval is initiated by a paced beat.

9. The method of claim 2, in which the third predetermined value is approximately between 350 milliseconds and 1000 milliseconds, and the third predetermined value is one of: (1) less than the first predetermined value, and (2) less than or equal to the first predetermined value.

10. The method of claim 1, in which the pacing the ventricle using the present indicated ventricular pacing interval is initiated by the detecting the atrial tachyarrhythmia.

11. The method of claim 1, in which the pacing the ventricle using the present indicated ventricular pacing interval is independent of the detecting the atrial tachyarrhythmia.

12. A method comprising:
   detecting an atrial tachyarrhythmia;
   stabilizing a ventricular heart rate, using an infinite impulse response filter to filter intervals between paced or sensed ventricular depolarizations to compute an indicated ventricular pacing interval on a beat-to-beat basis, in response to the detecting the atrial tachyarrhythmia;
   determining whether potentially proarrhythmic conditions exist; and
   delivering cardioversion/defibrillation therapy to the atrium, in response to the detecting the atrial tachyarrhythmia, if the determining whether potentially proarrhythmic conditions exist indicates that no potentially proarrhythmic conditions exist, otherwise withholding the delivery of cardioversion/defibrillation therapy to the atrium until no potentially proarrhythmic conditions exist.

13. The method of claim 12, in which the determining whether potentially proarrhythmic conditions exist comprises:
   comparing a most recent V—V interval to a first predetermined value;
      deeming no potentially proarrhythmic conditions to exist if the most recent V—V interval is longer than a first predetermined value;
      deeming no potentially proarrhythmic conditions to exist if the most recent V—V interval is shorter than the first predetermined value and the most recent V—V interval exceeds or equals a preceding V—V interval less a second predetermined value;
   deeming potentially proarrhythmic conditions to exist if the most recent V—V interval is shorter than a third predetermined value; and
      deeming potentially proarrhythmic conditions to exist if the most recent V—V interval is longer than the third predetermined value and the most recent V—V interval is shorter than the preceding V—V interval less the second predetermined value.

14. The method of claim 13, in which the determining whether potentially proarrhythmic conditions exist in the ventricle further comprises:
   deeming potentially proarrhythmic conditions to exist if the most recent V—V interval is equal to the third predetermined value; and
   deeming no potentially proarrhythmic conditions to exist if the most recent V—V interval is equal to the first predetermined value.

15. The method of claim 13, in which the first predetermined value is approximately between 700 milliseconds and 1000 milliseconds.

16. The method of claim 13, in which the first predetermined value is different when the most recent V—V interval is initiated by a sensed beat than when the most recent V—V interval is initiated by a paced beat.

17. The method of claim 13, in which the second predetermined value is approximately between 0 milliseconds and 200 milliseconds.

18. The method of claim 13, in which second predetermined value is different when the most recent V—V interval is initiated by a sensed beat than when the most recent V—V interval is initiated by a paced beat.

19. The method of claim 13, in which the third predetermined value is different when the most recent V—V interval is initiated by a sensed beat than when the most recent V—V interval is initiated by a paced beat.

20. The method of claim 13, in which the third predetermined value is approximately between 350 milliseconds and 1000 milliseconds, and the third predetermined value is one of: (1) less than the first predetermined value, and (2) less than or equal to the first predetermined value.

21. A cardiac rhythm management system, comprising:
an atrial heart signal sensing circuit;
a ventricular heart signal sensing circuit, configured to sense V—V intervals between ventricular depolarizations of a ventricle;
a ventricular pacing therapy circuit;
an atrial cardioversion/defibrillation therapy circuit; and
a controller, communicatively coupled to the atrial heart signal sensing circuit, the ventricular heart signal sensing circuit, the ventricular pacing therapy circuit, and the atrial cardioversion/defibrillation therapy circuit, the controller including:
a ventricular rate stabilization circuit, including an infinite impulse response (IIR) filter circuit outputting a variable indicated pacing interval, the IIR filter circuit using at least first input comprising a duration of a most recent sensed V—V interval and a second input comprising a preceding value of the indicated pacing interval; and
an atrial cardioversion/defibrillation control circuit that (a) determines if potentially proarrhythmic ventricular conditions exist, and (b) includes an atrial therapy circuit that delivers cardioversion/defibrillation therapy to the atrium if no potentially proarrhythmic conditions exist, and otherwise withholds the delivery of cardioversion/defibrillation therapy to the atrium.

22. The system of claim 21, further comprising a programmer, remote from and communicatively coupled to the controller.

23. The system of claim 21, further comprising a leadwire adapted for being coupled between at least one of: (1) a coronary sinus, and (2) a superior vena cava and an implantable device comprising the atrial and ventricular heart signal sensing circuits, the ventricular pacing and atrial cardioversion/defibrillation circuits, and the controller.

24. The system of claim 21, in which the controller includes an atrial tachyarrhythmia detection module, and in which the ventricular pacing therapy circuit is configured to initiate pacing of the ventricle at the variable indicated pacing interval, outputted by the IIR filter circuit, in response to an atrial tachyarrhythmia detected by the atrial tachyarrhythmia detection module.

25. A method comprising:
detecting an atrial tachyarrhythmia;
stabilizing a ventricular heart rate, using an infinite impulse response filter to compute an indicated ventricular pacing interval, in response to the detecting the atrial tachyarrhythmia;
determining whether potentially proarrhythmic conditions exist, including:
comparing a most recent V—V interval to a first predetermined value;
deeming no potentially proarrhythmic conditions to exist if the most recent V—V interval is longer than or equal to a first predetermined value;
deeming no potentially proarrhythmic conditions to exist if the most recent V—V interval is shorter than the first predetermined value and the most recent V—V interval exceeds or equals a preceding V—V interval less a second predetermined value;
deeming potentially proarrhythmic conditions to exist if the most recent V—V interval is shorter than or equal to a third predetermined value; and
deeming potentially proarrhythmic conditions to exist if the most recent V—V interval is longer than the third predetermined value and the most recent V—V interval is shorter than the preceding V—V interval less the second predetermined value; and
delivering cardioversion/defibrillation therapy to the atrium, in response to the detecting the atrial tachyarrhythmia, if the determining whether potentially proarrhythmic conditions exist indicates that no potentially proarrhythmic conditions exist, otherwise withholding the delivery of cardioversion/defibrillation therapy to the atrium until no potentially proarrhythmic conditions exist.

26. The method of claim 25, in which the using the infinite impulse response filter to compute the indicated ventricular pacing interval includes using the infinite impulse response filter to compute the indicated ventricular pacing interval on a beat-to-beat basis.

27. A method comprising:
detecting an atrial tachyarrhythmia;
stabilizing a ventricular heart rate, using an infinite impulse response filter to compute an indicated ventricular pacing interval, in response to the detecting the atrial tachyarrhythmia;
determining whether potentially proarrhythmic conditions exist, including:
comparing a most recent V—V interval to a first predetermined value, in which the first predetermined value is different when the most recent V—V interval is initiated by a sensed beat than when the most recent V—V interval is initiated by a paced beat;
deeming no potentially proarrhythmic conditions to exist if the most recent V—V interval is longer than a first predetermined value;
deeming no potentially proarrhythmic conditions to exist if the most recent V—V interval is shorter than the first predetermined value and the most recent V—V interval exceeds or equals a preceding V—V interval less a second predetermined value;
deeming potentially proarrhythmic conditions to exist if the most recent V—V interval is shorter than a third predetermined value; and
deeming potentially proarrhythmic conditions to exist if the most recent V—V interval is longer than the third predetermined value and the most recent V—V interval is shorter than the preceding V—V interval less the second predetermined value; and
delivering cardioversion/defibrillation therapy to the atrium, in response to the detecting the atrial tachyarrhythmia, if the determining whether potentially proarrhythmic conditions exist indicates that no potentially proarrhythmic conditions exist, otherwise withholding the delivery of cardioversion/defibrillation therapy to the atrium until no potentially proarrhythmic conditions exist.

28. The method of claim 27, in which the using the infinite impulse response filter to compute the indicated ventricular pacing interval includes using the infinite impulse response filter to compute the indicated ventricular pacing interval on a beat-to-beat basis.

29. A method comprising:

detecting an atrial tachyarrhythmia;

stabilizing a ventricular heart rate, using an infinite impulse response filter to compute an indicated ventricular pacing interval, in response to the detecting the atrial tachyarrhythmia;

determining whether potentially proarrhythmic conditions exist, including:

comparing a most recent V—V interval to a first predetermined value;

deeming no potentially proarrhythmic conditions to exist if the most recent V—V interval is longer than a first predetermined value;

deeming no potentially proarrhythmic conditions to exist if the most recent V—V interval is shorter than the first predetermined value and the most recent V—V interval exceeds or equals a preceding V—V interval less a second predetermined value, in which the second predetermined value is different when the most recent V—V interval is initiated by a sensed beat than when the most recent V—V interval is initiated by a paced beat;

deeming potentially proarrhythmic conditions to exist if the most recent V—V interval is shorter than a third predetermined value; and deeming potentially proarrhythmic conditions to exist if the most recent V—V interval is longer than the third predetermined value and the most recent V—V interval is shorter than the preceding V—V interval less the second predetermined value; and delivering cardioversion/defibrillation therapy to the atrium, in response to the detecting the atrial tachyarrhythmia, if the determining whether potentially proarrhythmic conditions exist indicates that no potentially proarrhythmic conditions exist, otherwise withholding the delivery of cardioversion/defibrillation therapy to the atrium until no potentially proarrhythmic conditions exist.

30. The method of claim 29, in which the using the infinite impulse response filter to compute the indicated ventricular pacing interval includes using the infinite impulse response filter to compute the indicated ventricular pacing interval on a beat-to-beat basis.

31. A method comprising:

detecting an atrial tachyarrhythmia;

stabilizing a ventricular heart rate, using an infinite impulse response filter to compute an indicated ventricular pacing interval, in response to the detecting the atrial tachyarrhythmia;

determining whether potentially proarrhythmic conditions exist, including:

comparing a most recent V—V interval to a first predetermined value;

deeming no potentially proarrhythmic conditions to exist if the most recent V—V interval is longer than a first predetermined value;

deeming no potentially proarrhythmic conditions to exist if the most recent V—V interval is shorter than the first predetermined value and the most recent V—V interval exceeds or equals a preceding V—V interval less a second predetermined value;

deeming potentially proarrhythmic conditions to exist if the most recent V—V interval is shorter than a third predetermined value, in which the third predetermined value is different when the most recent V—V interval is initiated by a sensed beat than when the most recent V—V interval is initiated by a paced beat; and deeming potentially proarrhythmic conditions to exist if the most recent V—V interval is longer than the third predetermined value and the most recent V—V interval is shorter than the preceding V—V interval less the second predetermined value; and delivering cardioversion/defibrillation therapy to the atrium, in response to the detecting the atrial tachyarrhythmia, if the determining whether potentially proarrhythmic conditions exist indicates that no potentially proarrhythmic conditions exist, otherwise withholding the delivery of cardioversion/defibrillation therapy to the atrium until no potentially proarrhythmic conditions exist.

32. The method of claim 31, in which the using the infinite impulse response filter to compute the indicated ventricular pacing interval includes using the infinite impulse response filter to compute the indicated ventricular pacing interval on a beat-to-beat basis.

* * * * *